United States Patent
Beshore et al.

(10) Patent No.: US 8,022,215 B2
(45) Date of Patent: Sep. 20, 2011

(54) FUSED PYRIDONE M1 RECEPTOR POSITIVE ALLOSTERIC MODULATORS

(75) Inventors: Douglas C. Beshore, Lower Gwynedd, PA (US); Robert M. DiPardo, Lansdale, PA (US); Scott D. Kuduk, Harleyville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/866,387

(22) PCT Filed: Feb. 4, 2009

(86) PCT No.: PCT/US2009/033022
§ 371 (c)(1),
(2), (4) Date: Aug. 5, 2010

(87) PCT Pub. No.: WO2009/102588
PCT Pub. Date: Aug. 20, 2009

(65) Prior Publication Data
US 2010/0324088 A1    Dec. 23, 2010

Related U.S. Application Data

(60) Provisional application No. 61/065,930, filed on Feb. 15, 2008.

(51) Int. Cl.
*A61P 25/28* (2006.01)
*A61P 25/00* (2006.01)
*A61P 29/00* (2006.01)

(52) U.S. Cl. ......... 546/156; 514/312; 514/299; 546/183

(58) Field of Classification Search .................. None
See application file for complete search history.

(56) References Cited

FOREIGN PATENT DOCUMENTS

| WO | WO 2004073639 | | 9/2004 |
|---|---|---|---|
| WO | WO 2007067489 A1 | * | 6/2007 |
| WO | WO 2007100366 | | 9/2007 |

OTHER PUBLICATIONS

R. M. Eglen et al., "Therapeutic Opportunities from Muscarinic Receptor Research", 2001, pp. 409-414, vol. 22, No. 8, Trends in Pharmacological Sciences.
A. Fischer, Therapeutic Strategies in Alzheimer's Disease: M1 Muscarinic Agonists, 2000, pp. 101-112, vol. 84, Jpn. J. Pharmacol.
T. A. Spalding et al., "Discovery of an Ectopic Activation Site on the M1 Muscarinic Receptor", 2002, pp. 1297-1302, Molecular Pharmacology.
S. Lazareno et al., "Analogs of WIN 62.577 Define a Second Allosteric Site on Muscarinic Receptors", 2002, pp. 1492-1505, vol. 62, Molecular Pharmacology.
S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site",2000, pp. 194-207, vol. 58, Molecular Pharmacology.
M. P. Caulfield, "Muscarinic Receptors-Characterization, Coupling and Function", 1993, pp. 319-379, vol. 58, Pharma. Ther.
N. J. M. Birdsall et al., "Multipel Allosteric Sites on Muscarinic Receptors", 2001, pp. 2517-2524, vol. 68, Life Sciences.
A. Christopoulos et al., "Allosteric Binding Sites on Cell-Surface Receptors: Novel Targets for Drug Discovery", 2002, pp. 198-210, Natural Reviews, Drug Discovery.
J. A. Goodwin et al, "Roof and Floor of the Muscarinic Binding Pocket: Variations in the Binding Modes of Orthosteric Ligands", 2007, pp. 1484-1496, vol. 72, Molecular Pharmacology.
F. Fanelli et al., "Theoretical Quantitative Structure-Activity Relationship Analysis on Three Dimensional Models of Ligand-m1 Muscarinic Receptor Complexes", 1994, pp. 195-211, vol. 2, Bioorganic & Medicinal Chemistry.

* cited by examiner

*Primary Examiner* — Janet Andres
*Assistant Examiner* — Timothy R Rozof
(74) *Attorney, Agent, or Firm* — Sylvia A. Ayler; Gerard M. Devlin

(57) ABSTRACT

The present invention is directed to fused pyridone compounds of formula (I) (I) that are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

15 Claims, No Drawings

FUSED PYRIDONE M1 RECEPTOR POSITIVE ALLOSTERIC MODULATORS

CROSS REFERENCE TO RELATED APPLICATIONS

This application is the National Stage of International Application No. PCT/US2009/033022 filed on Feb. 4, 2009, which claims the benefit under 35 U.S.C. 119(e) of U.S. Provisional Application No. 61/065,930, filed Feb. 15, 2008.

FIELD OF THE INVENTION

The invention is directed to a class of fused pyridone compounds, their salts, pharmaceutical compositions comprising them and their use in therapy of the human body. In particular, the invention is directed to a class of hydroxycycloalkane fused pyridone compounds, which are muscarinic M1 receptor positive allosteric modulators and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, as well as behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences*, 2001, 22:8, 409-414. In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol*, 2000, 84:101-112, However, M1 ligands that have been developed and studied for Alzheimer's Disease have produced side effects common to other muscarinic receptor ligands, such as sweating, nausea and diarrhea. See Spalding et al, *Mol Pharmacol*, 2002, 61:6, 1297-1302.

The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505; S. Lazareno et al, *Mol Pharmacol*, 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is novel fused pyridone compounds of generic formula (I)

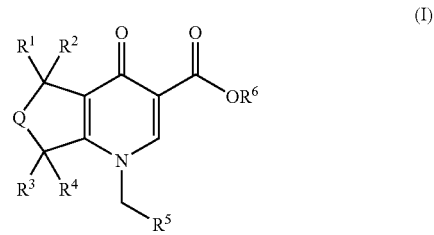

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I)

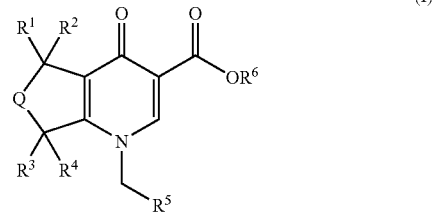

and pharmaceutically acceptable salts thereof, wherein
Q is selected from the group consisting of
(1) —$CH_2$—, or
(2) —$CH_2CH_2$—;

$R^1$ and $R^2$ are each selected from the group consisting of
(1) hydrogen,
(2) hydroxy,
(3) —$C_{1-6}$ alkyl,
(4) —$OC_{1-6}$ alkyl,
(5) —$C_{1-3}$ alkyl-$C_{6-10}$ aryl, or
(6) —$N(R^7R^8)$,
wherein any $R^1$ or $R^2$ alkyl or aryl moiety is optionally substituted with one or more halogen,
or $R^1$ and $R^2$ together form the group =O;
$R^3$ and $R^4$ are each selected from the group consisting of
(1) hydrogen,
(2) hydroxy,
(3) —$C_{1-6}$ alkyl, or
(4) —$OC_{1-6}$ alkyl,
or $R^3$ and $R^4$ together form the group =O;
$R^5$ is selected from the group consisting of
(1) —$CH_2$—$C_{6-10}$ aryl,
(2) —$C_{2-4}$alkenyl-$C_{6-10}$ aryl, or
(3) —$CH_2$-pyridyl,
wherein any $R^5$ aryl or pyridyl moiety is optionally substituted with one or more
  (a) halogen,
  (b) hydroxy,
  (c) cyano,
  (d) —$(CH_2)_q$-aryl,
  (e) —O—$(CH_2)_q$-aryl,
  (f) —$C_{1-6}$ alkyl,
  (g) —$OC_{1-6}$ alkyl,
  (h) heteroaryl, wherein said heteroaryl is an aromatic cyclic group having from 5 to 12 cyclic atoms, said cyclic atoms selected from carbon, nitrogen, oxygen or sulfur,
  (i) —$N(R^7R^8)$,
and wherein said alkyl, aryl or heteroaryl moiety is optionally substituted with one or more
  (i) halogen,
  (ii) hydroxy,
  (iii) cyano,
  (iv) —$C_{1-6}$ alkyl, or
  (v) —$OC_{1-6}$ alkyl;
$R^6$ is selected from the group consisting of
(1) hydrogen,
(2) —$C_{1-6}$ alkyl, and
(3) —$CH_2$-aryl,
wherein any $R^6$ alkyl or aryl moiety is optionally substituted with one or more
  (a) halogen,
  (b) cyano, and
  (c) —O—$C_{1-6}$ alkyl, wherein said alkyl is optionally substituted with one or more halo;
$R^7$ and $R^8$ are each selected from the group consisting of
(1) hydrogen,
(2) —$C_{1-6}$ alkyl,
(3) —$C_{1-3}$ alkyl-$C_{6-10}$ aryl,
and any $R^7$ or $R^8$ alkyl or aryl moiety is optionally substituted with one or more halogen, or $R^7$ and $R^8$ and the nitrogen atom to which they are both bonded are linked together to form a 5- or 6-membered ring; and
q is 0 or 1.

In particular embodiments of the compounds of formula (I), each of $R^1$, $R^2$, $R^3$ and $R^4$ is hydrogen.

In particular embodiments of the compounds of formula (I), $R^2$ is hydrogen or methyl.

In particular embodiments of the compounds of formula (I), $R^1$ and $R^2$ together form oxo.

In particular embodiments of the compounds of formula (I), both $R^1$ and $R^2$ together form oxo and $R^3$ and $R^4$ together form oxo.

In particular embodiments of the compounds of formula (I), $R^1$ and $R^2$ are each selected from the group consisting of
(1) hydrogen,
(2) hydroxy,
(3) —$C_{1-6}$ alkyl,
(4) —$OC_{1-6}$ alkyl,
(5) —$C_{1-3}$ alkyl-$C_{6-10}$ aryl, or
(6) —$N(R^7R^8)$,
wherein any $R^1$ or $R^2$ alkyl or aryl moiety is optionally substituted with one or more halogen,
or $R^1$ and $R^2$ together form the group =O;
and $R^3$ and $R^4$ are each hydrogen.

In particular embodiments of the compounds of formula (I), $R^1$ is selected from the group consisting of
(1) hydrogen,
(2) hydroxy,
(3) —$C_{1-6}$ alkyl,
(4) —$OC_{1-6}$ alkyl,
(5) —$C_{1-3}$ alkyl-$C_{6-10}$ aryl, or
(6) —$N(R^7R^8)$,
wherein any $R^1$ alkyl or aryl moiety is optionally substituted with one or more halogen,
and $R^2$, $R^3$ and $R^4$ are each hydrogen.

In particular embodiments of the compounds of formula (I), $R^5$ is selected from benzyl or —$CH_2$-pyridyl, wherein said phenyl or pyridyl moiety is optionally substituted with one or more
  (a) halogen,
  (b) hydroxy,
  (c) cyano,
  (d) —$(CH_2)_q$-aryl,
  (e) —O—$(CH_2)_q$-aryl,
  (f) —$C_{1-6}$ alkyl,
  (g) —$OC_{1-6}$ alkyl,
  (h) heteroaryl, wherein said heteroaryl is an aromatic cyclic group having from 5 to 12 cyclic atoms, said cyclic atoms selected from carbon, nitrogen, oxygen or sulfur,
  (m) —$N(R^7R^8)$,
and wherein said alkyl, aryl or heteroaryl moiety is optionally substituted with one or more
  (i) halogen,
  (ii) hydroxy,
  (iii) cyano,
  (iv) —$C_{1-6}$ alkyl, or
  (v) —$OC_{1-6}$ alkyl.

In particular embodiments of the compounds of formula (I), $R^6$ is hydrogen.

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, by combining a compound of formula (I) with one or more pharmaceutically acceptable carriers.

Within the genus of compounds of formula (I), there is a sub-genus of compounds of formula (II):

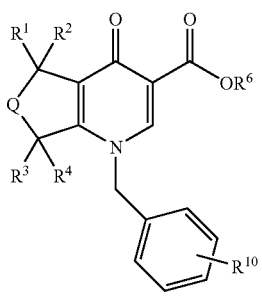

(II)

and pharmaceutically acceptable salts thereof, wherein $R^1$, $R^2$, $R^3$, $R^4$ and $R^6$ are as defined above, and $R^{10}$ is optionally present at one or more of the phenyl ring carbon atoms, and is selected from the group consisting of
  (1) halogen,
  (2) hydroxy,
  (3) cyano,
  (4) —$(CH_2)_q$-aryl,
  (5) —O—$(CH_2)_q$-aryl,
  (6) —$C_{1-6}$ alkyl,
  (7) —$OC_{1-6}$ alkyl,
  (8) heteroaryl, wherein said heteroaryl is an aromatic cyclic group having from 5 to 12 cyclic atoms, said cyclic atoms selected from carbon, nitrogen, oxygen or sulfur,
  (9) —$N(R^7R^8)$,
  and wherein any $R^{10}$ alkyl, aryl or heteroaryl moiety is optionally substituted with one or more
    (a) halogen,
    (b) hydroxy,
    (c) cyano,
    (d) —$C_{1-6}$ alkyl, or
    (e) —$OC_{1-6}$ alkyl.

Within the genus of compounds of formula (I), there is a sub-genus of compounds of formula (III):

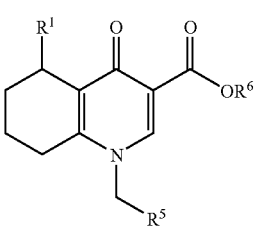

(III)

and pharmaceutically acceptable salts thereof, wherein $R^1$, $R^5$ and $R^6$ are as defined above.

Within the genus of compounds of formula (I), there is a sub-genus of compounds of formula (IV):

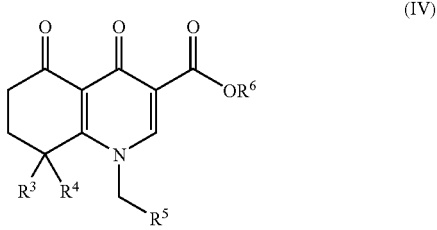

(IV)

and pharmaceutically acceptable salts thereof, wherein $R^3$, $R^4$, $R^5$ and $R^6$ are as defined above.

Specific embodiments of formula (I) are described herein as Examples 1-74, such as
  1-(Biphenyl-4-ylmethyl)-4-oxo-4,5,6,7-tetrahydro-1H-cyclopenta[b]pyridine-3-carboxylic acid;
  1-[(2E)-3-(2-Fluorophenyl)prop-2-en-1-yl]-4,5-dioxo-1,4,5,6,7,8-hexahydroquinoline-3-carboxylic acid;
  1-[(2Z)-3-(2-Fluorophenyl)prop-2-en-1-yl]-4,5-dioxo-1,4,5,6,7,8-hexahydroquinoline-3-carboxylic acid;
  1-(Biphenyl-4-ylmethyl)-5-hydroxy-4-oxo-1,4,5,6,7,8-hexahydroquinoline-3-carboxylic acid;
  (±)-5-Hydroxy-1-[(2'-methoxybiphenyl-4-yl)methyl]-4-oxo-1,4,5,6,7,8-hexahydroquinoline-3-carboxylic acid;
  (±)-1-(Biphenyl-4-ylmethyl)-5-methoxy-4-oxo-1,4,5,6,7,8-hexahydroquinoline-3-carboxylic acid;
  (±)-5-Hydroxy-5-methyl-1-(2-naphthylmethyl)-4-oxo-1,4,5,6,7,8-hexahydroquinoline-3-carboxylic acid;
  (±)-1-(Biphenyl-4-ylmethyl)-5-ethyl-5-hydroxy-4-oxo-1,4,5,6,7,8-hexahydroquinoline-3-carboxylic acid;
  (±)-5-benzyl-1-(biphenyl-4-ylmethyl)-5-hydroxy-4-oxo-1,4,5,6,7,8-hexahydroquinoline-3-carboxylic acid;
or a pharmaceutically acceptable salt thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) to (IV), or a pharmaceutically acceptable salt thereof.

The invention is also directed to the use of a compound of formulae (II) to (IV) for treating a disease or disorder in which the M1 receptor is involved, such as Alzheimer's Disease, cognitive impairment, schizophrenia, pain disorders and sleep disorders, by administering to the patient a compound of formulae (II) to (IV), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) to (IV), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, by combining a compound of formulae (II) to (IV), or a pharmaceutically acceptable salt thereof, with a pharmaceutically acceptable carrier.

Where a variable occurs more than once in any of Formulas (I) to (IV) or in a substituent thereof; the individual occurrences of that variable are independent of each other, unless otherwise specified.

As used herein, in particular in the definitions of $R^1$, $R^2$, $R^3$, $R^4$, $R^5$, $R^6$, $R^7$, $R^8$ and $R^{10}$, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, iso-butyl, tert-butyl, pentyl, hexyl, and the like. $C_0$ alkyl means a bond.

As used herein, in particular in the definition of $R^5$, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, in particular in the definitions of $R^1$, $R^2$, $R^5$, $R^6$, $R^7$, $R^8$ and $R^{10}$, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings, which are partially aromatic (i.e., one of the fused rings is aromatic and the other is non-aromatic). An exemplary aryl group that is partially aromatic is indynyl.

As used herein, the term "halo" or "halogen" includes fluoro, chloro, bromo and iodo.

As used herein, in particular in the definition of $R^5$, the term "heteroaryl," by itself or as part of another substituent, means a cyclic or polycyclic group having ring carbon atoms and at least one ring heteroatom (O, N or S), wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

Preferred $R^5$ heteroaryl groups have from 5 to 12 ring atoms, preferably from 5 to 10. In one such embodiment, the heteroaryl groups have 5 or 6 ring atoms.

For example, one subgroup of $R^5$ heteroaryl groups have 5 or 6 ring atoms and a single heteroatom, which is nitrogen. Exemplary heteroaryl groups in this embodiment are pyridyl and pyrrolyl.

Another subgroup of $R^5$ heteroaryl groups have 5 or 6 ring atoms and a single heteroatom, which is selected from sulfur and oxygen. Exemplary heteroaryl groups in this embodiment are thienyl and furanyl.

Another subgroup of $R^5$ heteroaryl groups have 5 or 6 ring atoms and two or three heteroatoms, which are selected from sulfur, oxygen and nitrogen. Exemplary heteroaryl groups in this embodiment are pyrazolyl, imidazolyl, isoxazolyl and triazolyl (such as 1,2,4-triazolyl).

Another subgroup of $R^5$ heteroaryl groups have 9 or 10 ring atoms and one or two heteroatoms, which are selected from oxygen, sulfur and nitrogen. Exemplary heteroaryl groups in this embodiment are indolyl, benzothiazolyl and quinoxalinyl.

The term "heteroaryl" also includes fused cyclic heterocyclic rings that are partially aromatic (i.e., one of the fused rings is aromatic and the other is non-aromatic). An exemplary heteroaryl group that is partially aromatic is benzodioxol.

When a heteroaryl group as defined herein is substituted, the substituent may be bonded to a ring carbon atom of the heteroaryl group or on a ring heteroatom (i.e., a nitrogen, oxygen or sulfur), which has a valence that permits substitution. Preferably, the substituent is bonded to a ring carbon atom. Similarly, when a heteroaryl group is defined as a substituent herein, the point of attachment may be at a ring carbon atom of the heteroaryl group or on a ring heteroatom (i.e., a nitrogen, oxygen or sulfur), which has a valence which permits attachment. Preferably, the attachment is at a ring carbon atom.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (IV).

Formulae (I) to (IV) are shown above without a definite stereochemistry at certain positions. The present invention includes all stereoisomers of formulae (I) to (IV) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction schemes, in which variables are as defined before or are derived, using readily available starting materials, from reagents and conventional synthetic procedures. It is also possible to use variants which are themselves known to those of ordinary skill in the art of organic synthesis, but are not mentioned in greater detail.

Ethyl 4-oxo-4,5,6,7-tetrahydro-1H-cyclopenta[b]pyridine-3-carboxylate (1a) and ethyl 4-oxo-1,4,5,6,7,8-hexahydroquinoline-3-carboxylate (1b) are known compounds (Scheme 1). Alkylation is carried out with the appropriate alkyl or benzyl halide in a solvent like DMF using a base like potassium carbonate. Hydrolysis of the ethyl ester can be affected using a base like sodium hydroxide in a solvent like ethanol to afford Example 1.

Scheme 1

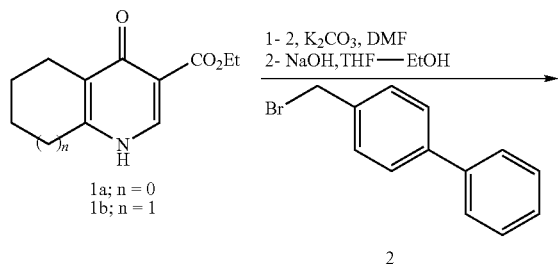

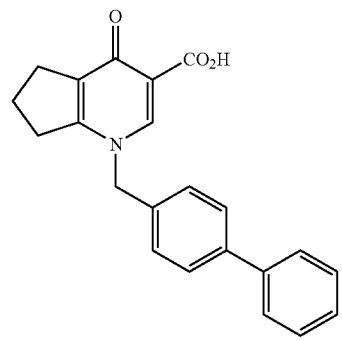

Example 1

Heating of 3 and 4 at the appropriate temperatures allows formation of 5. Alkylation of 5 with 2 according to Scheme 1 produces ester 6. Hydrolysis of 6 following Scheme 1 produces Example 6. Alternatively, the ketone present in 6 may be reduced using a reagent like sodium borohyride in a solvent like methanol, followed by ester hydrolysis to produce Example 17.

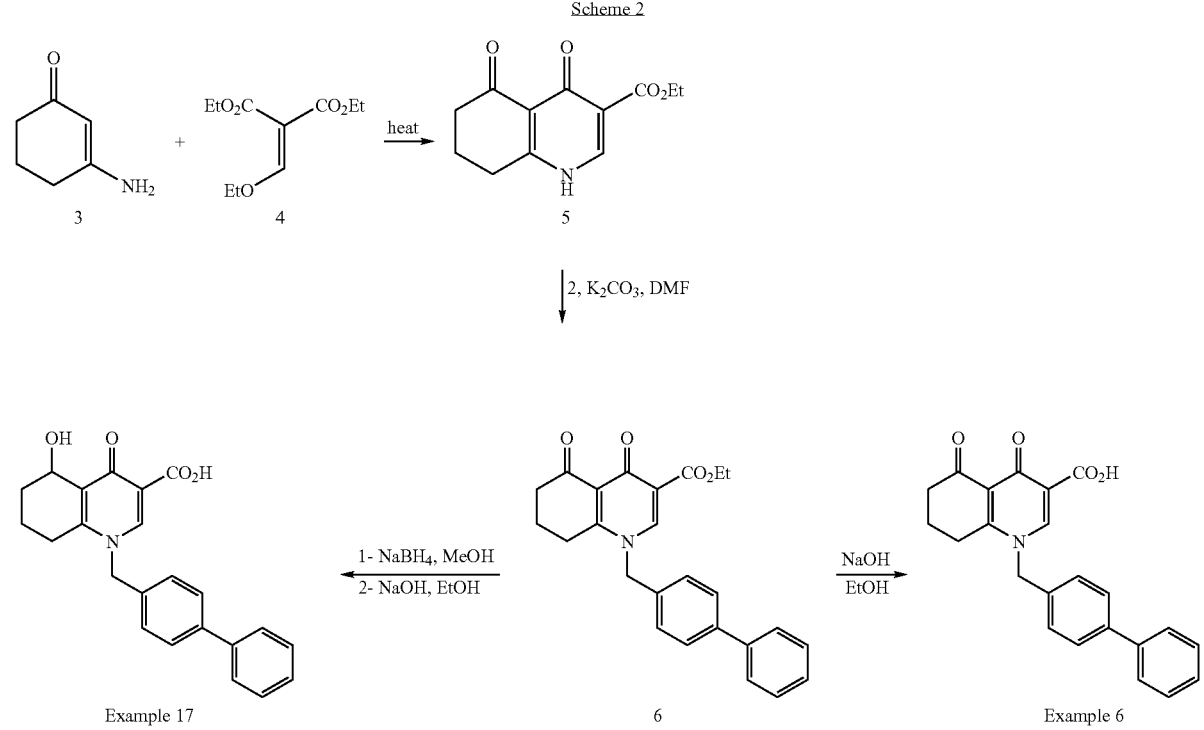

Ester 7 can be made using the alkylation procedure described in Scheme 1. Ester 7 can undergo a cross coupling with boronic acid 8 using a metal like palladium(0), a phosphine ligand such as 2-dicyclohexylphosphino-2',4',6'-triisopropylbiphenyl (X-Phos), with a base like potassium carbonate in a solvent like acetonitrile. Subsequent hydrolysis according to Scheme 1 produces Example 15.

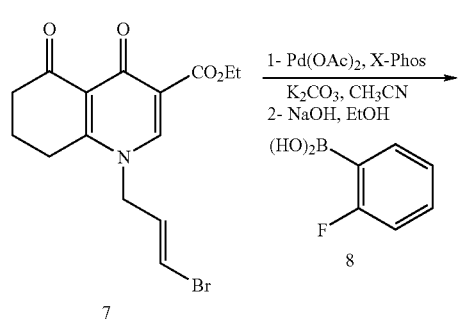

Ester 9 may be prepared as described in Schemes 1 and 2. Ester 9 can undergo a cross-coupling reaction with boronic acid 10 as described in Scheme 3 using a solvent like DMSO to produce Example 27 (Scheme 4).

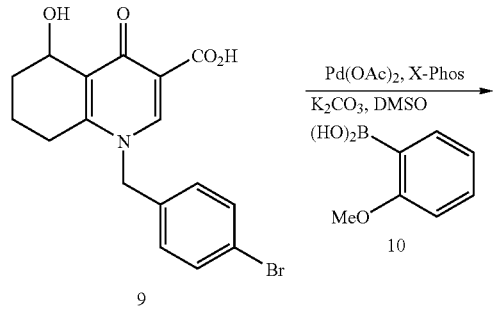

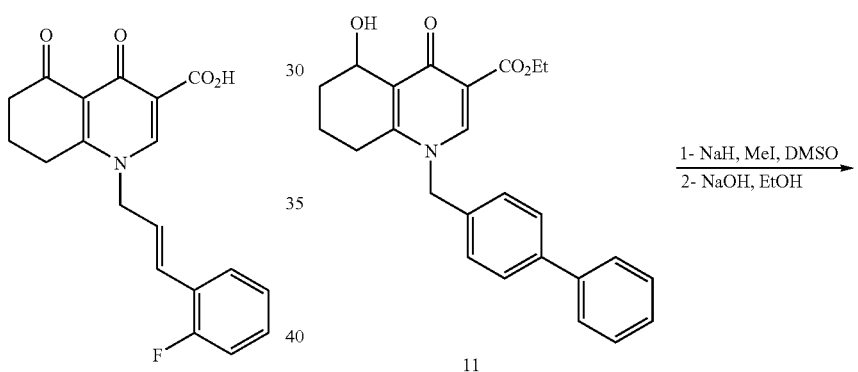

Compound 11 may be alkylated using the appropriate alkyl halide such as methyl iodide with a base like sodium hydride in a solvent such as DMSO. Subsequent hydrolysis following Scheme 1 affords Example 62 (Scheme 5).

Example 6 may undergo addition with an organometallic reagent such as ethylmagnesium bromide in a solvent like dichloromethane at an appropriate temperature (Scheme 6). Alternatively, reductive amination of Example 6 with an amine such as methylamine in a solvent like THF in the presense of acetic acid with a reducing agent like sodium triacetoxyborohydride provides Example 70.

Scheme 6

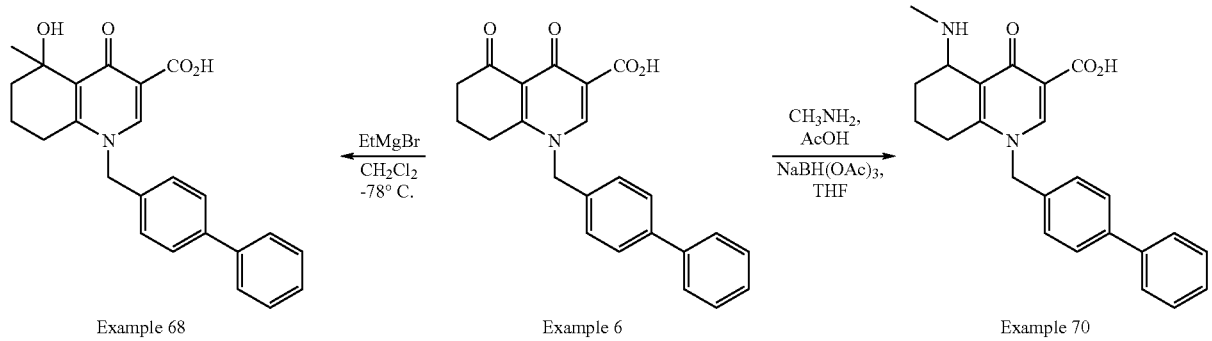

Example 68    Example 6    Example 70

The present invention also provides a method for the synthesis of compounds useful as intermediates in the preparation of compounds of the invention.

During any of the above synthetic sequences, it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1991. The protecting groups may be removed at a convenient sequent stage using methods known from the art.

Specific embodiments of the compounds of the invention and methods of making them are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505.

As used herein, the terms "positive allosteric modulator" and "allosteric potentiator" are used interchangeably and refer to a ligand that interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site that is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal form, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, rnandelic, methanesulfonic, mucic, nitric, pamoic, pantothenic, phosphoric, succinic, sulfuric, tartaric, p-toluenesulfonic acid, and the like.

The present invention is directed to the use of the compounds of formulae (I) to (IV) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early, intermediate or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketaniine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders and that these systems evolve with medical and scientific progress. Thus, the term "schizophrenia" or "psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, ariprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, α-2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents, when used in combination with the subject compound, may be in the form of a pharmaceutically acceptable salt, for example chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chiorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Potential sleep conditions or disorders for which the compounds of the invention may be useful include: enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e., stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift worker's sleep disturbances; dyssomnias; night terror; insomnias associated with depression, emotional/mood disorders, as well as sleep walking and enuresis, and sleep disorders that accompany aging; Alzheimer's sundowning; conditions associated with circadian rhythmicity as well as mental and physical disorders associated with travel across time zones and with rotating shift-work schedules, conditions due to drugs that cause reductions in REM sleep as a side effect; syndromes that are manifested by non-restorative sleep and muscle pain or sleep apnea that is associated with respiratory disturbances during sleep; and conditions that result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmenorhea, as well as pain associated with angina, and inflammatory pain of varied origins (e.g., osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists; ADAM 10 ligands or activators; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists; 5-HT6 antagonists; 5-HT1a antagonists; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies); antibiotics, such as doxycycline and rifampin; anti-inflammatory compounds such as (R)-flurbiprofen and nitroflurbiprofen; PPAR gamma agonists, such as pioglitazone and rosiglitazone; CB-1 receptor antagonists or CB-1 receptor inverse agonists; N-methyl-D-aspartate (NMDA) receptor antagonists, such as memantine and neramexane; cholinesterase inhibitors such as galantamine, rivastigmine, donepezil, tacrine and phenserine; growth hormone secretagogues such as ibutamoren, ibutamoren mesylate, and capromorelin; histamine $H_3$ receptor antagonists; AMPA agonists or AMPA modulators; PDE IV inhibitors; PDE 10 inhibitors; $GABA_A$ inverse agonists; $GABA_A$ α5 receptor ligands; $GABA_B$ receptor ligands; inverse agonists; glycogen synthase kinase 3β (GSK3β) inhibitors; neuronal nicotinic agonists; selective M1 agonists; HDAC inhibitors; MET kinase inhibitors; LCAT modulators; thrombin receptor antagonists;

NR2B antagonists; mGluR5 modulators; mGluR1 modulators; mGluR2 antagonists; potassium channel blockers; PI3k inhibitors; orexin receptor antagonists; IKKβ inhibitors; macrophage migration inhibitory factor inhibitors; and microtubule affinity regulating kinase (MARK) inhibitors; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B 1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXXIYY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, aloniniid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods, such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product that results, directly or indirectly, from combination of the specified ingredients in the specified amounts. This term in relation to pharmaceutical compositions is intended to encompass a product comprising one or more active ingredients and an optional carrier comprising inert ingredients, as well as any product that results, directly or indirectly, from combination, complexation or aggregation of any two or more of the ingredients or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion.

In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically palatable preparations. Tablets may contain the active ingredient in admixture with non-toxic pharmaceutically acceptable excipients that are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules, wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdennal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release faun. The total daily dosage is from about 1.0 rng to about 2,000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1,000 mg of the active ingredient, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1,000 mg, administered once, twice or three times per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the schemes and examples herein. Starting materials are made according to procedures known in the art or as illustrated herein. The following examples are provided so that the invention might be more fully understood, and are not to be construed as limiting the scope of the invention in any manner.

EXAMPLE 1

1-(Biphenyl-4-ylmethyl)-4-oxo-4,5,6,7-tetrahydro-1H-cyclopenta[b]pyridine-3-carboxylic acid Ethyl 4-oxo-4,5,6,7-tetrahydro-1H-cyclopenta[b]pyridine-3-carboxylate (302 mg, 1.46 mmol) was dissolved in N,N-dimethylformamide (3 mL) and treated with 4-bromomethylbiphenyl (432 mg, 1.75 mmol, 1.2 equiv) and potassium carbonate (242 mg, 1.75 mmol, 1.2 equiv). The mixture was stirred at ambient temperature under an atmosphere of nitrogen for 18 hours. The mixture was poured into water and extracted three times with ethyl acetate. The combined ethyl acetate extracts were washed once with water and brine and then dried with sodium sulfate, filtered and concentrated in vacuo, providing ethyl-(1-biphenyl-4-ylmethyl)-4-oxo-4,4a,5,6,7,7a-hexahydro-1H-cyclopenta[b]pyridine-3-carboxylate.

The above ethyl carboxylate (544 mg, 1.46 mmol) was dissolved in absolute ethanol (5 mL) and was treated with sodium hydroxide (1.75 mL, 1 N aqueous, 1.2 equiv). The mixture was stirred at ambient temperature for 2 hrs and then acidified (≦pH 4) with hydrochloric acid (1 N aqueous). The precipitate that formed was collected and washed successively with water and absolute ethanol, providing the title compound as a white solid: $^1$H-NMR (400 MHz, CDCl$_3$) δ 8.52 (1H, s), 7.63 (2H, d, J=8.2 Hz) 7.57 (2H, d, J=7.0 Hz), 7.46 (2H, t, J=7.1 Hz), 7.18 (2H, d, J=8.2 Hz), 5.18 (2H, s), 2.99-2.93 (4H, m), 2.22-2.15 (2H, m) ppm; high resolution mass spectrum (ES+) m/z 346.1442 [(M+H)$^+$; calculated for $C_{22}H_{20}NO_3$: 346.1438].

The following compounds were prepared according to the general procedure described in Example 1, substituting with ethyl 4-oxo-1,4,5,6,7,8-hexahydroquinoline-3-carboxylate (Examples 2-5), with ethyl 4,5-dioxo-1,4,5,6,7,8-hexahydroquinoline-3-carboxylate (Examples 6-12) or with ethyl 4,8-dioxo-1,4,5,6,7,8-hexahydroquinoline-3-carboxylate (Examples 13-14). The starting materials are either commercially available, known in the literature or may be prepared from commercially available reagents using conventional reactions well known in the art.

| Ex. | R$^1$ | R$^2$ | R$^3$ | HRMS/LRMS |
|---|---|---|---|---|
| 2 | H, H | H, H | 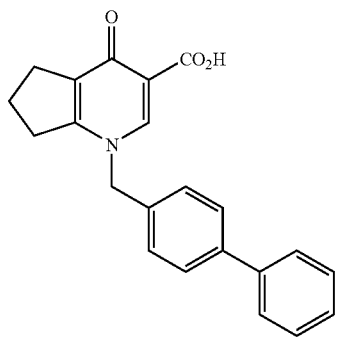 | $C_{23}H_{22}NO_3$ [M + H] Calc. 360.1594 Obs. 360.1606 |

-continued

[Structure: quinoline with R¹, R² on fused ring positions, 4-oxo, 3-CO₂H, N-CH(wavy)-CH₂-R³]

| Ex. | R¹ | R² | R³ | HRMS/LRMS |
|---|---|---|---|---|
| 3 | H, H | H, H | 2-naphthyl-CH₂- | C₂₁H₂₀NO₃ [M + H] LRMS: 334.2 |
| 4 | H, H | H, H | 4-methoxyphenyl-CH₂- | C₁₈H₂₀NO₄ [M + H] LRMS: 314.2 |
| 5 | H, H | H, H | 4-(1H-pyrazol-1-yl)phenyl-CH₂- | C₂₀H₂₀N₃O₃ [M + H] LRMS: 350.1 |
| 6 | O | H, H | 4-biphenyl-CH₂- | C₂₃H₂₀NO₄ [M + H] LRMS: 374.2 |
| 7 | O | H, H | 3-biphenyl-CH₂- | C₂₃H₂₀NO₄ [M + H] Calc. 374.1387 Obs. 374.1377 |

-continued

[Structure: same quinoline scaffold]

| Ex. | R¹ | R² | R³ | HRMS/LRMS |
|---|---|---|---|---|
| 8 | O | H, H | 4-(1H-pyrazol-1-yl)phenyl-CH₂- | C₂₀H₁₈N₃O₄ [M + H] LRMS: 364.1 |
| 9 | O | H, H | 4-(1H-pyrazol-1-yl)phenyl-CH₂- | C₂₀H₁₈N₃O₄ [M + H] LRMS: 364.1 |
| 10 | O | H, H | 2-naphthyl-CH₂- | C₂₁H₁₈NO₄ [M + H] LRMS: 348.1 |
| 11 | O | H, H | 4-phenoxyphenyl-CH₂- | C₂₃H₂₀NO₄ [M + H] Calc. 390.1336 Obs. 390.1353 |
| 12 | O | H, H | 4-(1H-1,2,4-triazol-1-yl)phenyl-CH₂- | C₁₉H₁₇N₄O₄ [M + H] LRMS: 365.1 |

-continued

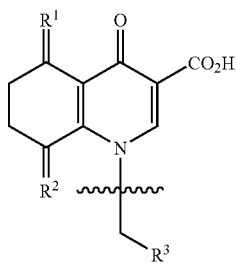

| Ex. | R¹ | R² | R³ | HRMS/LRMS |
|---|---|---|---|---|
| 13 | H, H | O | <br>![structure with OCH3 benzyl] | $C_{18}H_{18}NO_5$ [M + H] LRMS: 328.3 |
| 14 | H, H | O | <br>![biphenyl structure] | $C_{23}H_{20}NO_4$ [M + H] Calc. 374.1387 Obs. 374.1387 |

EXAMPLE 15

1-[(2E)-3-(2-Fluorophenyl)prop-2-en-1-yl]-4,5-dioxo-1,4,5,6,7,8-hexahydroquinoline-3-carboxylic acid

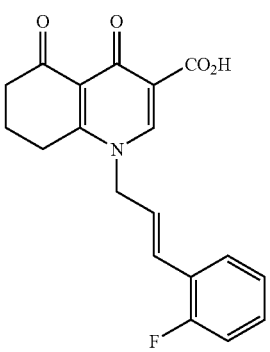

Ethyl-4,5-dioxo-1,4,5,6,7,8-hexahydroquinoline-3-carboxylate (714 mg, 3.04 mmol) was suspended in degassed N,N-dimethylformamide (8 mL) and treated with 1,3-dibromo-1-propene (0.364 mL, 3.64 mmol, 1.2 equiv) and potassium carbonate (503 mg, 3.64 mmol, 1.2 equiv). After stirring for 7 hrs at ambient temperature, the mixture was poured into water and extracted three times with ethyl acetate. The combined ethyl acetate extracts were washed once with water and brine, dried with sodium sulfate, filtered and concentrated in vacuo to afforded ethyl 1-[3-bromoprop-2-en-1-yl]-4,5-dioxo-1,4,5,6,7,8-hexahydroquinoline-3-carboxylate as a mixture of E- and Z-isomers. Additional compound was obtained by concentration of the aqueous extract in vacuo and extraction of the resulting residue with a mixture of 80% chloroform and 20% methanol (v/v).

The above bromopropenyl hexahydroquinoline carboxylate (314 mg, 0.887 mmol) was dissolved in acetonitrile (2 mL) and treated with 2-fluorophenylboronic acid (248 mg, 1.77 mmol, 2.0 equiv), an aqueous solution (0.2 mL) of potassium carbonate (306 mg, 2.22 mmol, 2.5 equiv) and X-Phos (51 mg, 0.106 mmol, 0.12 equiv). The mixture was degassed, placed under a nitrogen atmosphere and treated with palladium (II) acetate (8 mg, 0.04 mmol, 0.045 equiv). After stirring at ambient temperature for 3 hrs, the mixture was concentrated in vacuo and the resulting residue was partitioned between water and ethyl acetate. The aqueous layer was extracted thrice with ethyl acetate and the combined organic extracts were washed once with brine, dried with sodium sulfate, filtered and concentrated in vacuo. The residue was purified by silica gel chromatography, eluting with 0 to 5% methanol in chloroform, to afford ethyl 1-[3-(2-fluorophenyl)prop-2-en-1-yl]-4,5-dioxo-1,4,5,6,7,8-hexahydroquinoline-3-carboxylate as a mixture of E- and Z-isomers.

The above mixture of E- and Z-ethyl carboxylates (60 mg, 0.16 mmol) was dissolved in absolute ethanol (2 mL) and treated with lithium hydroxide (0.19 mL, 1 N aqueous, 1.2 equiv). After stirring at ambient temperature for 1 hr, the mixture was rendered acidic ($\leq$pH 4) with hydrochloric acid (1 N aqueous). The mixture was concentrated in vacuo and the residue was purified via preparative reverse phase HPLC, providing the title compound as the less polar product: $^1$H-NMR (400 MHz, CDCl$_3$) δ 8.57 (1H, s), 7.40 (1H, t, J=7.9 Hz), 7.30 (1H, q, J=6.0 Hz), 7.17-7.06 (2H, m), 6.65 (1H, d, J=16.0 Hz), 6.36 (1H, m), 4.88 (2H, s), 3.07 (2H, br s), 2.64 (2H, br s), 2.20 (2H, br s) ppm; liquid chromatography/mass spectrometry (ES+) m/z 342.1 [(M+H)$^+$; calculated for $C_{19}H_{17}FNO_4$: 342.3].

EXAMPLE 16

1-[(2Z)-3-(2-Fluorophenyl)prop-2-en-1-yl]-4,5-dioxo-1,4,5,6,7,8-hexahydroquinoline-3-carboxylic acid

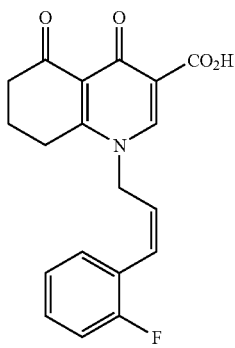

Using the procedure described in Example 15, the title compound was isolated by preparative reverse phase HPLC as the more polar product: $^1$H-NMR (400 MHz, CDCl$_3$) δ 8.48 (1H, s), 7.39 (1H, m), 7.26-7.14 (3H, m), 6.85 (1H, d, J=11.4 Hz), 5.83 (1H, m), 4.81 (2H, br s), 2.79 (2H, br s), 2.57

(2H, br s), 2.10 (2H, br s) ppm; liquid chromatography/mass spectrometry (ES+) m/z 342.1 [(M+H)+, calculated for $C_{19}H_{17}FNO_4$: 342.3].

EXAMPLE 17

1-(Biphenyl-4-ylmethyl)-5-hydroxy-4-oxo-1,4,5,6,7,8-hexahydroquinoline-3-carboxylic acid

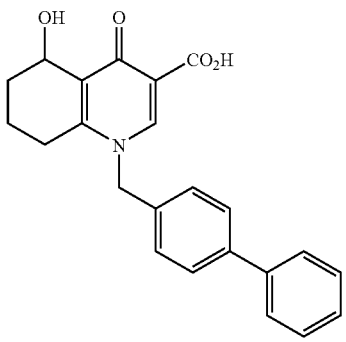

Diethyl ethoxymethylenemalonate (6.42 g, 29.7 mmol) and 3-aminocyclohex-2-en-1-one (3 g, 27 mmol) were combined and placed into an oil bath preheated to 130° C. for 14 hrs. The mixture was concentrated in vacuo and the residue was purified by silica gel chromatography, eluting with 15 to 40% ethyl acetate in hexanes, to afford diethyl {[3-oxocyclohex-1-en-1-yl)amino]methylene)malonate.

The above cyclohexenyl aminomethylene malonate (3.00 g, 10.7 mmol) was dissolved in diphenyl ether (18 mL) and placed into an oil bath preheated to 220° C. for 2 hrs. The reaction mixture was cooled to ambient temperature and diluted with two volumes of hexanes. The solid that precipitated was collected by filtration, washed with hexanes and dried under vacuum to afford ethyl 4,5-dioxo-1,4,5,6,7,8-hexahydroquinoline-3-carboxylate as an off-white solid.

To the above ethyl carboxylate (3.10 g, 13.2 mmol) in degassed dimethylformamide (50 mL) was added 4-bromomethylbiphenyl (3.91 g, 15.8 mmol, 1.2 equiv) and potassium carbonate (2.19 g, 15.8 mmol, 1.2 equiv). The mixture was stirred at ambient temperature for 4 hrs and then poured into water and ethyl acetate. The solid that formed was collected by filtration, washed with water and ethyl acetate and dried under vacuum to provide ethyl 1-(biphenyl-4-ylmethyl)-4,5-dioxo-1,4,5,6,7,8-hexahydroquinoline-3-carboxylate.

The above prepared ethylbiphenylmethyl carboxylate (357 mg, 0.889 mmol) was suspended in tetrahydrofuran (4 mL) and methanol (5 mL) under an atmosphere of nitrogen. Sodium borohydride (16.8 mg, 0.445 mmol) was added and the mixture was stirred at ambient temperature for 30 mins. The mixture was concentrated in vacuo and the residue purified by silica gel chromatography, eluting with 0 to 6% methanol in chloroform, to provide racemic ethyl 1-(biphenyl-4-ylmethyl)-5-hydroxy-4-oxo-1,4,5,6,7,8-hexahydroquinoline-3-carboxylate.

The above racemic biphenylmethyl hydroxyhexahydroquinoline carboxylate (138 mg, 0.342 mmol) was dissolved in absolute ethanol and treated with sodium hydroxide (0.410 mL, 1 N aqueous, 1.2 equiv). After stirring at ambient temperature for 2 hrs, the mixture was rendered acidic (≦pH 4) with hydrochloric acid (1 N aqueous). The solid that formed was collected by filtration and washed successively with water and ethanol and then dried under vacuum to afford the title compound: $^1$H-NMR (400 MHz, d$^6$-DMSO) δ 8.94 (1H, s), 7.67 (4H, dd, J=8.3, 8.0 Hz), 7.47 (2H, in), 7.37 (1H, m), 7.24 (2H, d, J=8.2 Hz), 5.57 (2H, dd, J=16.4, 11.1 Hz), 4.98 (1H, d, J=4.6 Hz), 4.88 (1H, d, J=3.8 Hz), 2.80 (1H, m), 1.87-1.87-1.71 (3H, m), 1.53-1.43 (1H, m) ppm; liquid chromatography/mass spectrometry (ES+) m/z 376.1 [(M+H)+, calculated for $C_{23}H_{22}NO_4$: 376.4].

The following compounds were prepared according to the general procedure described in Example 17, employing either ethyl 4,5-dioxo-1,4,5,6,7,8-hexahydroquinoline-3-carboxylate or ethyl 4,8-dioxo-1,4,5,6,7,8-hexahydroquinoline-3-carboxylate. The starting materials are either commercially available, known in the literature or may be prepared from commercially available reagents using conventional reactions well known in the art.

| Ex. | R$^1$ | R$^2$ | R$^3$ | HRMS/LRMS |
|---|---|---|---|---|
| 18 | H, OH | H, H | 2-naphthylmethyl | $C_{21}H_{20}NO_4$ [M + H] LRMS: 350.1 |
| 19 | H, OH | H, H | 4-(1,2,4-triazol-1-yl)benzyl | $C_{19}H_{19}N_4O_4$ [M + H] LRMS: 367.1 |
| 20 | H, OH | H, H | 4-(pyrazol-1-yl)benzyl | $C_{20}H_{20}N_3O_4$ [M + H] LRMS: 366.1 |

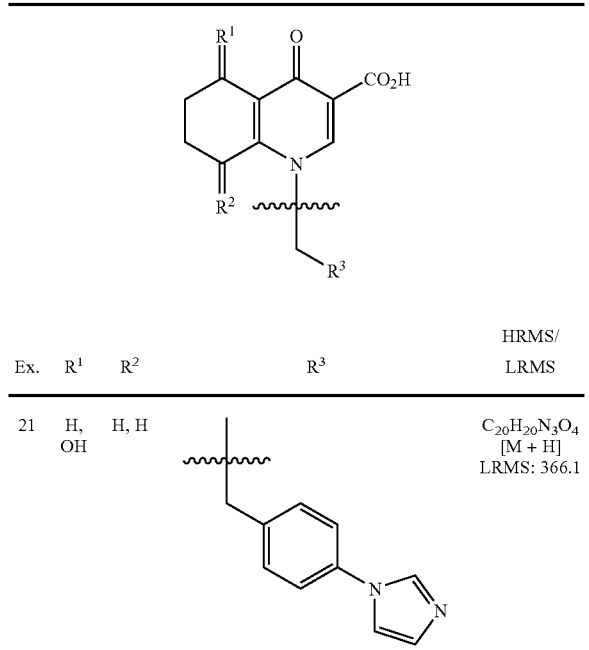

| Ex. | R¹ | R² | R³ | HRMS/LRMS |
|---|---|---|---|---|
| 21 | H, OH | H, H | 4-(imidazol-1-yl)benzyl | C₂₀H₂₀N₃O₄ [M + H] LRMS: 366.1 |
| 22 | H, OH | H, H | 3-biphenylmethyl | C₂₃H₂₂NO₄ [M + H] LRMS: 376.1 |
| 23 | H, OH | H, H | 4-phenoxybenzyl | C₂₃H₂₂NO₅ [M + H] Calc. 392.1493 Obs. 392.1496 |
| 24 | H, OH | H, H | (5-bromopyridin-2-yl)methyl | C₁₆H₁₆NO₄ [M + H] LRMS: 379.0 |
| 25 | H, H | H, OH | 4-methoxybenzyl | C₁₈H₂₀NO₅ [M + H] LRMS: 330.2 |

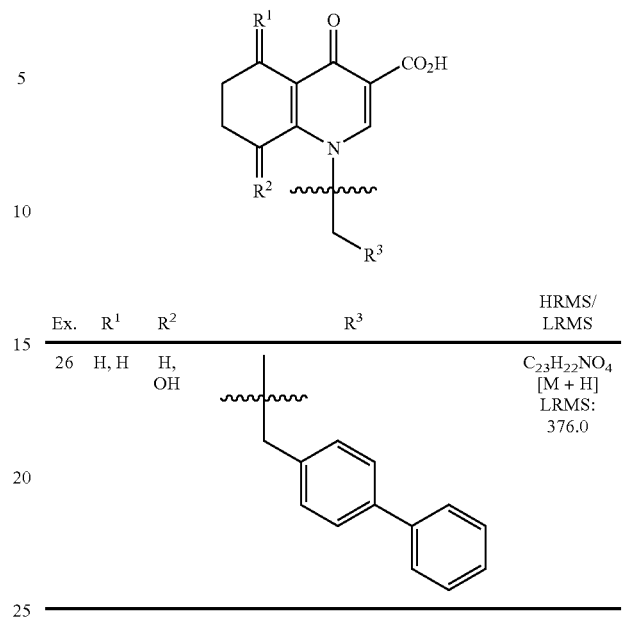

| Ex. | R¹ | R² | R³ | HRMS/LRMS |
|---|---|---|---|---|
| 26 | H, H | H, OH | 4-biphenylmethyl | C₂₃H₂₂NO₄ [M + H] LRMS: 376.0 |

EXAMPLE 27

(±)-5-Hydroxy-1-[(2'-methoxybiphenyl-4-yl)methyl]-4-oxo-1,4,5,6,7, 8-hexahydroquinoline-3carboxylic acid

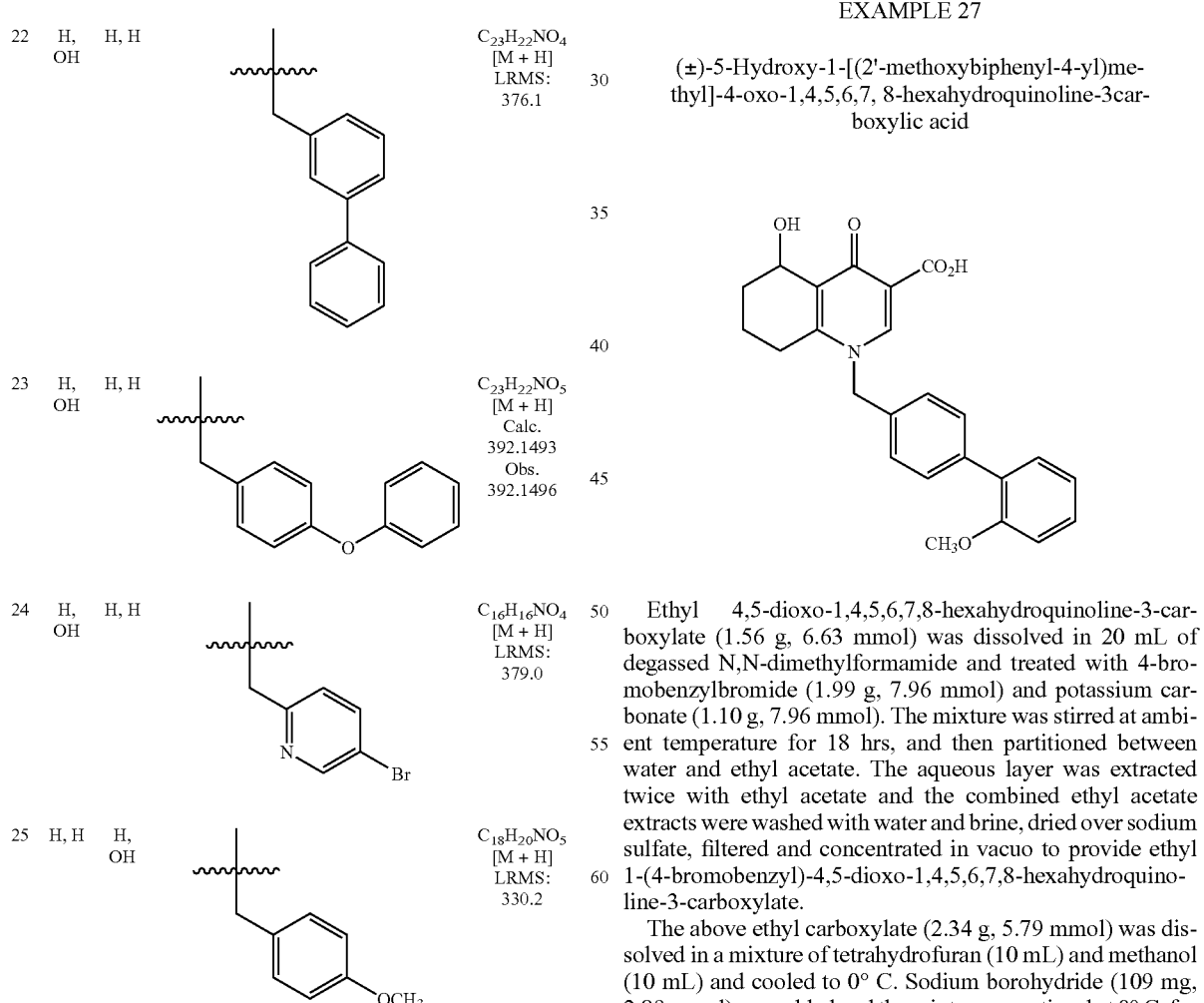

Ethyl 4,5-dioxo-1,4,5,6,7,8-hexahydroquinoline-3-carboxylate (1.56 g, 6.63 mmol) was dissolved in 20 mL of degassed N,N-dimethylformamide and treated with 4-bromobenzylbromide (1.99 g, 7.96 mmol) and potassium carbonate (1.10 g, 7.96 mmol). The mixture was stirred at ambient temperature for 18 hrs, and then partitioned between water and ethyl acetate. The aqueous layer was extracted twice with ethyl acetate and the combined ethyl acetate extracts were washed with water and brine, dried over sodium sulfate, filtered and concentrated in vacuo to provide ethyl 1-(4-bromobenzyl)-4,5-dioxo-1,4,5,6,7,8-hexahydroquinoline-3-carboxylate.

The above ethyl carboxylate (2.34 g, 5.79 mmol) was dissolved in a mixture of tetrahydrofuran (10 mL) and methanol (10 mL) and cooled to 0° C. Sodium borohydride (109 mg, 2.89 mmol) was added and the mixture was stirred at 0° C. for 5 minutes and then at rt for 30 mins. The mixture was concentrated in vacua and the residue was partitioned between water and ethyl acetate. The combined ethyl acetate extracts were washed once with brine, dried over sodium sulfate, filtered and concentrated. The residue was purified via silica gel chromatography, eluting with 0 to 5% methanol in chloroform, to afford ethyl 1-(4-bromobenzyl)-5-hydroxy-4-oxo-1,4,5,6,7,8-hexahydroquinoline-3-carboxylate.

The above hexahydroquinoline carboxylate (668 mg, 1.64 mmol) was treated with sodium hydroxide (1.81 mL, 1 N aqueous) in a mixture of absolute ethanol (4 mL) and tetrahydrofuran (4 mL). After stirring for 1 hr at 55° C., the reaction was rendered acidic (≦pH 4) with hydrochloric acid (1N aqueous). The mixture was concentrated in vacuo and the residue was then concentrated once from toluene (25 mL) to afford 1-(4-bromobenzyl)-5-hydroxy-4-oxo-1,4,5,6,7,8-hexahydroquinoline-3-carboxylic acid.

A 2-dram screw-cap vial was charged with the above carboxylic acid (51 mg, 0.13 mmol), X-Phos (7.7 mg, 0.016 mmol), 2-methoxyphenyl boronic acid (32 mg, 0.21 mmol), and dimethyl sulfoxide (1 mL). The mixture was stirred vigorously and potassium carbonate (46 mg, 0.33 mmol) in 0.2 mL of water was added along with palladium (II) acetate (3.6 mg, 0.0053 mmol). The mixture was heated at 80° C. for 90 minutes, cooled to ambient temperature and filtered. The mixture was purified via preparative reverse phase HPLC to provide the titled compound: $^1$H-NMR (500 MHz, d$^6$-DMSO) δ 8.93 (1H, s), 7.51 (2H, d, J=10.4 Hz), 7.35 (1H, t, J=7.4 Hz), 7.28 (1H, d, J=7.4 Hz), 7.17 (2H, d, J=8.9 Hz), 7.11 (1H, d, J=7.4 Hz), 7.02 (1H, t, J=7.4 Hz), 5.59 (1H, d, J=16.3 Hz), 5.52 (1H, d, J=16.3 Hz), 4.89 (1H, br s), 3.75 (3H, s), 2.83 (1H, m), 1.87 (1H, m), 1.79-1.73 (2H, m), 1.48 (1H, m) ppm; high resolution mass spectrum (ES+) m/z 406.1631 [(M+H)$^+$; calculated for $C_{24}H_{24}NO_5$: 406.1649].

The following compounds were prepared according to the general procedure described in Example 27, employing 1-(4-bromobenzyl)-5-hydroxy-4-oxo-1,4,5,6,7,8-hexahydroquinoline-3-carboxylic acid. The starting materials are either commercially available, known in the literature or may be prepared from commercially available reagents using conventional reactions well known in the art.

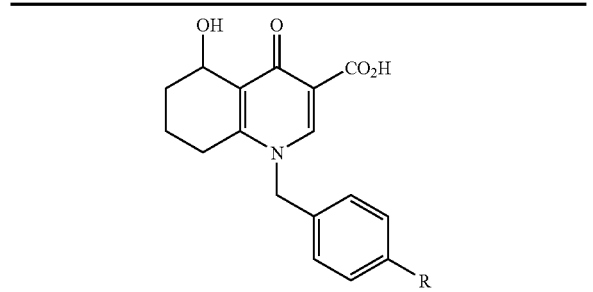

| Ex. | R | HRMS/LRMS |
|---|---|---|
| 28 | 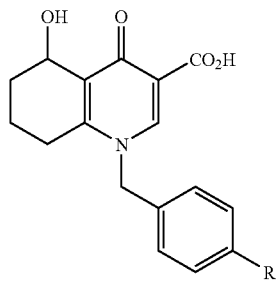 | $C_{24}H_{24}NO_6S$ [M + H] Calc. 454.1319 Obs. 454.1314 |
| 29 | 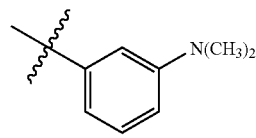 | $C_{23}H_{23}N_2O_4$ [M + H] Calc. 391.1653 Obs. 391.1647 |
| 30 | 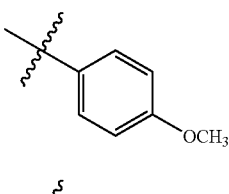 | $C_{25}H_{27}N_2O_4$ [M + H] Calc. 419.1966 Obs. 419.1966 |
| 31 | 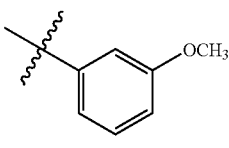 | $C_{24}H_{24}NO_5$ [M + H] Calc. 406.1649 Obs. 406.1643 |
| 32 | 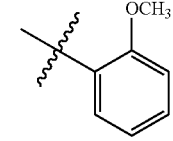 | $C_{24}H_{24}NO_5$ [M + H] LRMS: 406.2 |
| 33 | 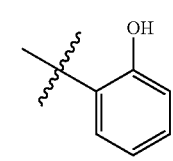 | $C_{24}H_{24}NO_5$ [M + H] Calc. 406.1649 Obs. 406.1631 |
| 34 | 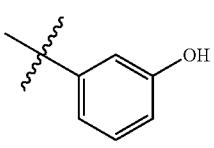 | $C_{23}H_{22}NO_5$ [M + H] Calc. 392.1493 Obs. 392.1467 |
| 35 | 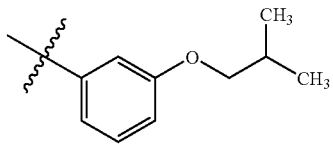 | $C_{23}H_{22}NO_5$ [M + H] Calc. 392.1493 Obs. 392.1470 |
| 36 | 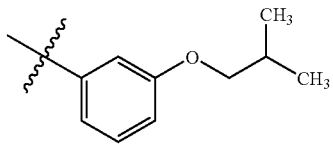 | $C_{27}H_{30}NO_5$ [M + H] Calc. 448.2119 Obs. 448.2094 |
| 37 | 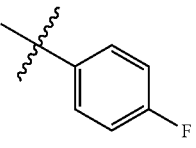 | $C_{23}H_{21}FNO_4$ [M + H] Calc. 394.1449 Obs. 394.1445 |

| Ex. | R | HRMS/LRMS |
|---|---|---|
| 38 | 4-Cl-phenyl | C₂₃H₂₁ClNO₄ [M + H] LRMS: 410.1 |
| 39 | 3-Cl-phenyl | C₂₃H₂₁ClNO₄ [M + H] Calc. 410.1154 Obs. 410.1134 |
| 40 | 2-Cl-phenyl | C₂₃H₂₁ClNO₄ [M + H] LRMS: 410.1 |
| 41 | 4-CN-phenyl | C₂₄H₂₁N₂O₄ [M + H] Calc. 401.1496 Obs. 401.1473 |
| 42 | 3-CN-phenyl | C₂₄H₂₁N₂O₄ [M + H] Calc. 401.1496 Obs. 401.1473 |
| 43 | 4-NHC(O)CH₃-phenyl | C₂₅H₂₅N₂O₅ [M + H] Calc. 433.1758 Obs. 433.1752 |
| 44 | 3-NHC(O)CH₃-phenyl | C₂₅H₂₅N₂O₅ [M + H] Calc. 433.1758 Obs. 433.1764 |
| 45 | 1-naphthyl | C₂₇H₂₄NO₄ [M + H] Calc. 426.17 Obs. 426.1693 |
| 46 | 4-COCH₃-phenyl | C₂₅H₂₄NO₅ [M + H] Calc. 418.1649 Obs. 418.1648 |
| 47 | 4-iBu-phenyl | C₂₇H₃₀NO₄ [M + H] Calc. 432.2170 Obs. 432.2143 |
| 48 | 2-CONH₂-phenyl | C₂₄H₂₃N₂O₅ [M + H] LRMS: 419.2 |
| 49 | 6-F-pyridin-3-yl | C₂₂H₂₀FN₂O₄ [M + H] Calc. 395.1402 Obs. 395.1396 |
| 50 | 3-CH₃-phenyl | C₂₄H₂₄NO₄ [M + H] Calc. 390.1700 Obs. 390.1695 |
| 51 | 6-NH₂-pyridin-3-yl | C₂₂H₂₂N₃O₄ [M + H] Calc. 392.1605 Obs. 392.1600 |
| 52 | 6-N(CH₃)₂-pyridin-3-yl | C₂₄H₂₆N₃O₄ [M + H] Calc. 420.1918 Obs. 420.1917 |
| 53 | 6-OCH₃-pyridin-3-yl | C₂₃H₂₃N₂O₅ [M + H] Calc. 407.1602 Obs. 407.1581 |

-continued

| Ex. | R | HRMS/LRMS |
|---|---|---|
| 54 | [indole, 5-substituted] | $C_{25}H_{23}N_2O_4$ [M + H] Calc. 415.1653 Obs. 415.1647 |
| 55 | [benzothiophene] | $C_{25}H_{22}NO_4S$ [M + H] Calc. 432.1264 Obs. 432.1260 |
| 56 | [1-methyl-pyrazol-4-yl] | $C_{21}H_{22}N_3O_4$ [M + H] Calc. 380.1605 Obs. 380.1602 |
| 57 | [1-isobutyl-pyrazol-4-yl] | $C_{24}H_{23}N_3O_4$ [M + H] Calc. 422.2075 Obs. 422.2055 |
| 58 | [thiophen-2-yl] | $C_{21}H_{20}NO_4S$ [M + H] Calc. 382.1108 Obs. 382.1109 |
| 59 | [thiophen-3-yl] | $C_{21}H_{20}NO_4S$ [M + H] Calc. 382.1108 Obs. 382.1105 |
| 60 | [furan-3-yl] | $C_{21}H_{29}NO_5$ [M + H] Calc. 366.1336 Obs. 366.1316 |

-continued

| Ex. | R | HRMS/LRMS |
|---|---|---|
| 61 | [3,5-dimethyl-isoxazol-4-yl] | $C_{22}H_{23}N_2O_5$ [M + H] Calc. 395.1602 Obs. 395.1582 |

EXAMPLE 62

(±)-1-(Biphenyl-4-ylmethyl)-5-methoxy-4-oxo-1,4,5,6,7,8-hexahydroquinoline-3-carboxylic acid

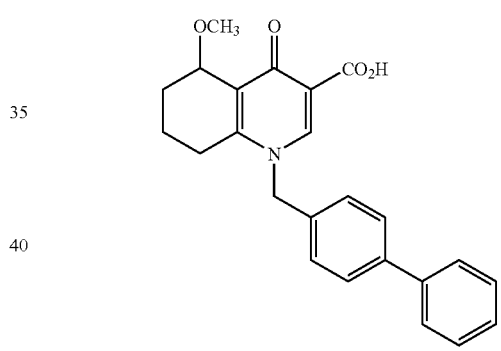

Racemic ethyl 1-(biphenyl-4-ylmethyl)-5-hydroxy-4-oxo-1,4,5,6,7,8-hexahydroquinoline-3-carboxylate (Example 17, 174 mg, 0.431 mmol) was dissolved in degassed N,N-dimethylformamide (2 mL), cooled to 0° C. under an atmosphere of nitrogen and treated with sodium hydride (19 mg, 0.47 mmol, 60% dispersion in mineral oil, 1.1 equiv) and then methyl iodide (0.096 mL, 1.55 mmol, 3.6 equiv). After stirring for 15 min, the mixture was warmed to ambient temperature and stirred for an additional 1 hr. The reaction mixture was poured into water and extracted three times with ethyl acetate. The combined ethyl acetate extracts were washed once with water and brine, dried with sodium sulfate, filtered and concentrated in vacuo to provide racemic ethyl 1-(biphenyl-4-ylmethyl)-5-methoxy-4-oxo-1,4,5,6,7,8-hexahydroquinoline-3-carboxylate.

The above ethyl carboxylate (174 mg, 0.417 mmol) was dissolved in absolute ethanol (3 mL) and treated with sodium hydroxide (0.417 mL, 1 N aqueous, 1.0 equiv). The mixture was stirred at ambient temperature for 2 hrs and then rendered acidic (≦pH 4) with hydrochloric acid (1N aqueous). The mixture was concentrated in vacuo and the residue was purified via preparative reverse phase HPLC to afford the title compound: $^1$H-NMR (500 MHz, d$^6$-DMSO) δ 8.63 (1H, s), 7.61 (2H, d, J=8.3 Hz), 7.57 (2H, d, J=8.5 Hz), 7.46 (2H, m), 7.38 (1H, m), 7.13 (2H, d, J=8.3 Hz), 5.24 (2H, s), 4.67 (1H, s), 3.53 (3H, s), 2.77 (1H, d, J=17.6 Hz), 2.54 (1H, m), 1.85 (1H, br s) ppm; liquid chromatography/mass spectrometry (ES+) m/z 390.2 [(M+H)$^+$, calculated for $C_{24}H_{24}NO_4$: 390.4].

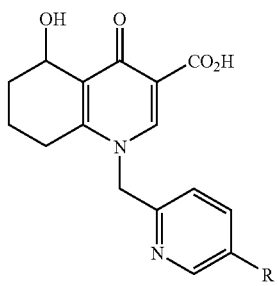

| Ex. | R | LRMS |
|---|---|---|
| 63 | (3-aminophenyl) | $C_{22}H_{22}N_3O_4$ [M + H] LRMS: 392.1 |
| 64 | (4-fluorophenyl) | $C_{22}H_{20}FN_2O_4$ [M + H] LRMS: 395.1 |
| 65 | (3-thienyl) | $C_{20}H_{19}N_2O_4S$ [M + H] LRMS: 383.1 |
| 66 | (1-methylindol-5-yl) | $C_{25}H_{24}N_3O_4$ [M + H] LRMS: 430.2 |

EXAMPLE 67

(±)-5-Hydroxy-5-methyl-1-(2-naphthylmethyl)-4-oxo-1,4,5,6,7,8-hexahydroquinoline-3-carboxylic acid

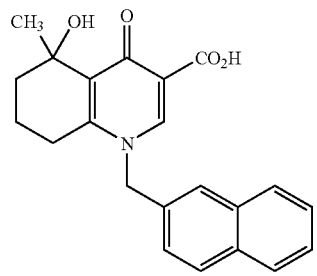

Example 10 (16 mg, 0.046 mmol) was dissolved in dichloromethane (5 mL) and cooled to −78° C. Methyl lithium (0.072 mL, 1.6 M solution in tetrahydrofuran, 2.5 equiv) was added dropwise and the mixture was stirred at −78° C. for 2 hrs. The reaction mixture was treated with methanol (1 mL) and hydrochloric acid (1 drop from a 9" pipette, 12 N aqueous) and then warmed to ambient temperature. The mixture was concentrated in vacuo and the resulting residue was purified via preparative reverse phase HPLC to provide the title compound: $^1$H-NMR (500 MHz, CDCl$_3$) δ 8.69 (1H, s), 7.91 (1H, d, J=8.4 Hz), 7.87 (1H, dd, J=6.1, 3.5 Hz), 7.81 (1H, dd, J=6.0, 3.5 Hz), 7.58-7.54 (2H, m), 7.44 (1H, br s), 7.17 (1H, dd, J=8.5, 1.7 Hz), 5.40 (1H, d, J=16.7 Hz), 5.36 (1H, d, J=16.5 Hz), 4.44 (1H, br s), 2.75 (1H, ddd, J=17.5, 5.0, 2.3 Hz), 2.62 (1H, ddd, J=17.2, 10.9, 6.3 Hz), 2.00-1.91 (2H, m), 1.85-1.80 (1H, m), 1.75-1.69 (1H, m), 1.66 (3H, s) ppm; high resolution mass spectrum (ES+) m/z 364.1554 [(M+H)$^+$; calculated for $C_{22}H_{22}NO_4$: 364.1544].

EXAMPLE 68

(±)-1-(Biphenyl-4-ylmethyl)-5-ethyl-5-hydroxy-4-oxo-1,4,5,6,7,8-hexahydroquinoline-3-carboxylic acid

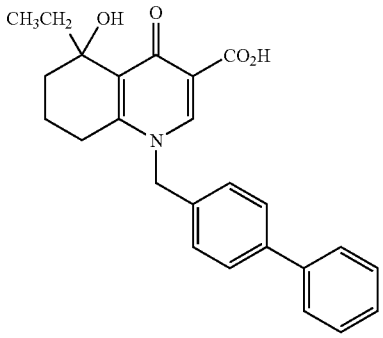

Example 6 (58 mg, 0.15 mmol) was dissolved in dichloromethane (5 mL) and cooled to −78° C. Ethyl magnesium bromide (0.13 mL, 3.0 M solution in tetrahydrofuran, 2.6 equiv) was added dropwise and the reaction mixture was stirred for 30 mins at −78° C. After treatment with methanol (1 mL) and hydrochloric acid (2 drops from a 9" pipette, 12 N aqueous), the mixture was warmed to ambient temperature and then concentrated in vacuo. The residue was purified by preparative reverse phase HPLC to provide the title compound: $^1$H-NMR (500 MHz, d$^6$-DMSO) δ 8.96 (1H, s), 7.71 (2H, d, J=8.2 Hz), 7.65 (2H, d, J=7.7 Hz), 7.47 (2H, t, J=7.7 Hz), 7.37 (1H, t, J=7.2 Hz), 7.27-7.22 (2H, m), 5.59 (2H, s), 5.23 (1H, br s), 2.77-2.63 (2H, m), 2.04-1.97 (1H, m), 1.88-1.74 (3H, m), 1.65-1.56 (1H, m), 1.46 (1H, t, J=14.6 Hz), 0.81 (3H, t, J=7.4 Hz) ppm; high resolution mass spectrum (ES+) m/z 404.1852 [(M+H)$^+$; calculated for $C_{25}H_{26}NO_4$: 404.1857].

EXAMPLE 69

(±)-5-benzyl-1-(biphenyl-4-ylmethyl)-5-hydroxy-4-oxo-1,4,5,6,7,8-hexahydroquinoline-3-carboxylic acid

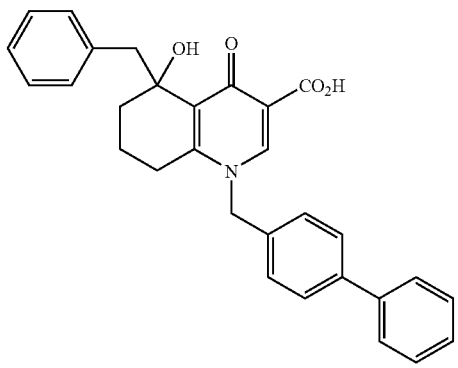

Example 6 (56 mg, 0.15 mmol) was dissolved in dichloromethane (5 mL) and cooled to −78° C. Benzylmagnesium chloride (0.19 mL, 2.0 M solution in tetrahydrofuran, 2.5 equiv) was added dropwise and the reaction mixture was stirred at −78° C. for 45 mins. After treatment with methanol (1 mL) and hydrochloric acid (2 drops from a 9" pipette, 12 N aqueous), the mixture was warmed to ambient temperature and then concentrated in vacuo. The residue was purified by preparative reverse phase HPLC to provide the title compound: $^1$H-NMR (500 MHz, d$^6$-DMSO) δ 9.01 (1H, s), 7.69 (2H, d, J=8.4 Hz), 7.66 (2H, d, J=7.1 Hz), 7.48 (2H, t, J=7.3 Hz), 7.38 (1H, t, J=7.0 Hz), 7.25 (2H, t, J=7.3 Hz), 7.22-7.15 (5H, m), 5.63 (1H, d, J=16.4 Hz), 5.53 (1H, d, J=16.8 Hz), 3.51 (1H, br s), 3.30 (1H, d, J=13.5 Hz), 3.22 (1H, d, J=14.1 Hz), 2.73-2.64 (1H, m), 2.61-2.54 (1H, m), 1.74-1.59 (3H, m), 1.41 (1H, t, J=11.6 Hz) ppm; high resolution mass spectrum (ES+) m/z 466.2031 [(M+H)$^+$; calculated for $C_{30}H_{28}NO_4$: 466.2013].

Using the following representative procedure, Examples 70 to 74 were prepared: Example 6 (50 mg, 0.14 mmol) and 4 Å molecular sieves (100 mg, 2 weight equiv) were suspended in acetonitrile (3 mL), to which was sequentially added acetic acid (0.023 mL, 0.40 mmol, 3 equiv), methyl amine (0.13 mL, 2.0 M solution in tetrahydrofuran) and sodium triacetoxyborohydride (51 mg, 0.24 mmol, 1.8 equiv). After stirring for 45 minutes at ambient temperature, methanol (1 mL) and hydrochloric acid (5 drops from a 9" pipette, 12 N aqueous) were added and the mixture was stirred at ambient temperature for an additional 45 minutes. The mixture was concentrated in vacuo and the residue was purified by preparative reverse phase HPLC to provide Example 70: $^1$H-NMR (500 MHz, d$^6$-DMSO) δ 9.10 (1H, s), 8.49 (1H, br m), 8.38 (1H, br m), 7.72 (2H, d, J=8.4 Hz), 7.66 (2H, d, J=7.0 Hz), 7.47 (2H, t, J=7.4 Hz), 7.38 (1H, t, J=7.4 Hz), 7.29 (2H, d, J=8.2 Hz), 5.66 (1H, d, J=16.1 Hz), 5.61 (1H, d, J=16.1 Hz), 4.45 (1H, br m), 2.83 (1H, d, J=18.6 Hz), 2.76-2.69 (1H, m), 2.69-2.63 (3H, m), 2.07-2.01 (1H, m), 1.85-1.78 (3H, m) ppm.

| Ex. | R | HRMS |
|---|---|---|
| 70 | CH$_3$—NH— | $C_{24}H_{25}N_2O_3$ [M + H] calc. 389.1860 obs. 389.1855 |
| 71 | CH$_3$(CH$_2$)$_3$NH— | $C_{27}H_{30}N_2O_3$ [M + H] calc. 431.2329 obs. 431.2327 |
| 72 | PhCH$_2$NH— | $C_{30}H_{29}N_2O_3$ [M + H] calc. 465.2173 obs. 465.2162 |
| 73 | pyrrolidin-1-yl | $C_{27}H_{28}N_2O_3$ [M + H] calc. 429.2173 obs. 429.2171 |
| 74 | piperidin-1-yl | $C_{29}H_{33}N_2O_3$ [M + H] calc. 457.2486 obs. 457.2476 |

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR$^{384}$ Fluorometric Imaging Plate Reader System. The assay studies the effect of one or several concentrations of test compounds on basal or acetylcholine-stimulated Ca$^{2+}$ levels using FLIPR.

Compounds are prepared and subjected to a preincubation period of 4 min. Thereafter, a single EC$_{20}$ concentration of acetylcholine is added to each well (3 nM final). The intracellular Ca$^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 µL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 µg/ml hygromycin is added.

Equipment: 384 well plate, 120 µL addition plate; 96-well Whatman 2 ml Uniplate Incubator, 37° C., 5% CO$_2$; Skatron EMBLA-384 Plate Washer; Multimek Pipetting System; Genesis Freedom 200 System; Mosquito System; Temo Nanolitre Pipetting System; and FLIPR$^{384}$ Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1N aqueous NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 µM in buffer for a final concentration of 1 µM in Assay. 20% Pluronic Acid Solution stock, with a concentration of 0.04% in Buffer, 0.02% in Assay.

65 µL of 2 mM Fluo-4AM are mixed with 130 µL of 20% Pluronic Acid. The resulting solution and 650 µL FBS is added to the assay buffer for a total volume of 65 mL. Positive Controls: 4-Br-A23187: 10 mM in DMSO; final concentration 10 µM. Acetylcholine: 10 mM in water, working stock at both 20 µM and 30 µM in assay buffer, final concentration of 10 µM. This is used to check the maximum stimulation of the CHOK1/hM1 cells. 20 µM (2×) acetylcholine is added in the preincubation part of the assay, and the 30 µM (3×) stock is added in the second part. (EC$_{20}$)Acetylcholine: 10 mM in water, working stock of 9 nM (3×), and final concentration in assay is 3 nM. This is used after the preincubation with test compounds. Addition of the EC$_{20}$ acetylcholine to each well with a test compound will ascertain any modulator activity. 24 wells contain 3 nM acetylcholine alone as a control.

Determining Activity of Putative Compounds:

Screening Plate: Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanolitre Pipetting System by transferring 1 µl of serial diluted compounds to each well, and 1 mM acetylcholine (100× stock concentration) were added as a control. Using Temo, 49 µl assay buffer is added to each well of the 384-well plate right before assay.

In a 96-well Whatman 2 ml Uniplate, 9 nM acetylcholine (3×) is pipetted into wells corresponding to the screening compounds and into control wells. The 30 µM acetylcholine control (3×) is added into control wells and the 3× agonist plate is transferred into a 384-well plate.

Cells are washed three times with 100 µL of buffer, leaving 30 µL of buffer in each well. Using Multimek, 30 µL of Dye Loading Buffer is added into each well and incubated at 37° C., 5% CO$_2$ for up to one hr.

After 60 min, the cells are washed three times with 100 µL of buffer, leaving 30 µL of buffer in each well. The cell plate, screening plate, and agonist addition plates are placed on the platform in the FLIPR and the door is closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the EC$_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 µM (10,000 nM) or less. The inflection point is calculated from the FLIPR values and is a measure of activity. Such a result is indicative of the intrinsic activity of the compounds as M1 allosteric modulators.

IP values from the aforementioned assay for representative exemplary compounds of the invention (as described herein) are provided below:

| Example | IP Value (nM) |
|---|---|
| 1 | 812 |
| 6 | 806 |
| 15 | 64000 |
| 17 | 450 |
| 27 | 3140 |
| 41 | 318 |
| 53 | 323 |
| 57 | 199 |
| 62 | 1100 |
| 66 | 199 |
| 68 | 9049 |
| 70 | 8371 |
| 71 | 1497 |
| 72 | 2200 |
| 73 | 4100 |
| 74 | 383 |

The following abbreviations are used throughout the text:
Me: methyl
Et: ethyl
t-Bu: tent-butyl
Ar: aryl
Ph: phenyl
Bn: benzyl
Ac: acetyl
DMSO: dimethylsulfoxide
DMEM: Dulbecco's Modified Eagle Medium (High Glucose)
FBS: fetal bovine serum
rt: room temperature
hr: hour
minute
aq: aqueous
HPLC: high performance liquid chromatography
MS: mass spectrometry
X-Phos: 2-dicyclohexylphosphino-2,4',6'-triisopropylbiphenyl While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. Therefore, it is intended that the invention be defined by the scope of the claims that follow and that such claims be interpreted as broadly as is reasonable.

What is claimed is:

1. A compound of formula (I):

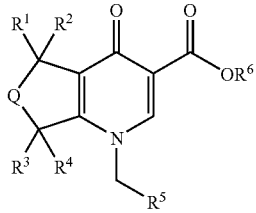

or a pharmaceutically acceptable salt thereof, wherein
Q is selected from the group consisting of
(2) —$CH_2CH_2$—;
$R^1$ and $R^2$ are each selected from the group consisting of
(1) hydrogen,
(2) hydroxy,
(3) —$C_{1-6}$ alkyl,
(4) —$OC_{1-6}$ alkyl,
(5) —$C_{1-3}$ alkyl-$C_{6-10}$ aryl, or
(6) —$N(R^7R^8)$,
wherein any $R^1$ or $R^2$ alkyl or aryl moiety is optionally substituted with one or more halogen,
or $R^1$ and $R^2$ together form the group =O;
$R^3$ and $R^4$ are each selected from the group consisting of
(1) hydrogen,
(2) hydroxy,
(3) —$C_{1-6}$ alkyl, or
(4) —$OC_{1-6}$ alkyl,
or $R^3$ and $R^4$ together form the group =O;
$R^5$ is selected from the group consisting of
(1) —$CH_2$—$C_{6-10}$ aryl,
(2) —$C_{2-4}$ alkenyl-$C_{6-10}$ aryl, or
wherein any $R^5$ aryl moiety is optionally substituted with one or more
(a) halogen,
(b) hydroxy,
(c) cyano,
(d) —$(CH_2)_q$-aryl,
(e) —O—$(CH_2)_q$-aryl,
(f) —$C_{1-6}$ alkyl,
(g) —$OC_{1-6}$ alkyl,
(h) heteroaryl, wherein said heteroaryl is an aromatic cyclic group having from 5 to 12 cyclic atoms, said cyclic atoms selected from carbon, nitrogen, oxygen or sulfur,
(i) —$N(R^7R^8)$,
and wherein said alkyl, aryl or heteroaryl moiety is optionally substituted with one or more
(i) halogen,
(ii) hydroxy,
(iii) cyano,
(iv) —$C_{1-6}$ alkyl, or
(v) —$OC_{1-6}$ alkyl,
$R^6$ is selected from the group consisting of
(1) hydrogen,
(2) —$C_{1-6}$ alkyl, and
(3) —$CH_2$-aryl,
wherein any $R^6$ alkyl or aryl moiety is optionally substituted with one or more
(a) halogen,
(b) cyano, and
(c) —O—$C_{1-6}$ alkyl, wherein said alkyl is optionally substituted with one or more halo;
$R^7$ and $R^8$ are each selected from the group consisting of
(1) hydrogen,
(2) —$C_{1-6}$ alkyl,
(3) —$C_{1-3}$ alkyl-$C_{6-10}$ aryl,
and any $R^7$ and $R^8$ alkyl or aryl moiety is optionally substituted with one or more halogen,
or $R^7$ and $R^8$ and the nitrogen atom to which they are both bonded are linked together to form a 5- or 6-membered ring; and
q is 0 or 1.

2. A compound of claim 1, or a pharmaceutically acceptable salt thereof, wherein
each of $R^1$, $R^2$, $R^3$ and $R^4$ is hydrogen.

3. A compound of claim 1, or a pharmaceutically acceptable salt thereof,
wherein $R^2$ is hydrogen or methyl.

4. A compound of claim 1, or a pharmaceutically acceptable salt thereof, wherein $R^1$ and $R^2$ together form oxo.

5. A compound of claim 4 or a pharmaceutically acceptable salt thereof, wherein
$R^1$ and $R^2$ together form oxo and $R^3$ and $R^4$ together form oxo.

6. A compound of claim 1, or a pharmaceutically acceptable salt thereof, wherein $R^1$ and $R^2$ are each selected from the group consisting of
(1) hydrogen,
(2) hydroxy,
(3) —$C_{1-6}$ alkyl,
(4) —$OC_{1-6}$ alkyl,
(5) —$C_{1-3}$ alkyl-$C_{6-10}$ aryl, or
(6) —$N(R^7R^8)$,
wherein any $R^1$ or $R^2$ alkyl or aryl moiety is optionally substituted with one or more halogen,
or $R^1$ and $R^2$ together form the group =O;
and $R^3$ and $R^4$ are each hydrogen.

7. A compound of claim 1, or a pharmaceutically acceptable salt thereof, wherein $R^1$ is selected from the group consisting of
(1) hydrogen,
(2) hydroxy,
(3) —$C_{1-6}$ alkyl,
(4) —$OC_{1-6}$ alkyl,
(5) —$C_{1-3}$ alkyl-$C_{6-10}$ aryl, or
(6) —$N(R^7R^8)$,
wherein any $R^1$ alkyl or aryl moiety is optionally substituted with one or more halogen,
and $R^2$, $R^3$ and $R^4$ are each hydrogen.

8. A compound of any of claim 1, or a pharmaceutically acceptable salt thereof, wherein $R^5$ is selected from benzyl, wherein said phenyl moiety is optionally substituted with one or more
(a) halogen,
(b) hydroxy,
(c) cyano,
(d) —$(CH_2)_q$-aryl,
(e) —O—$(CH_2)_q$-aryl,
(f) —$C_{1-6}$ alkyl,
(g) —$OC_{1-6}$ alkyl,
(h) heteroaryl, wherein said heteroaryl is an aromatic cyclic group having from 5 to 12 cyclic atoms, said cyclic atoms selected from carbon, nitrogen, oxygen or sulfur;
(i) —$N(R^7R^8)$,
and wherein said alkyl, aryl or heteroaryl moiety is optionally substituted with one or more (i) halogen,
(ii) hydroxy,
(iii) cyano,
(iv) —$C_{1-6}$ alkyl, or
(v) —$OC_{1-6}$ alkyl.

9. A compound of any of claim 1, or a pharmaceutically acceptable salt thereof, wherein $R^6$ is hydrogen.

10. A compound of claim 1, wherein the compound of formula (I) is a compound of formula (II):

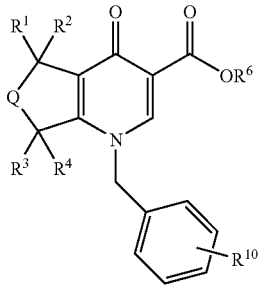

(II)

or a pharmaceutically acceptable salt thereof, wherein Q, $R^1$, $R^2$, $R^3$, $R^4$ and $R^6$ are as in claim 1, and $R^{10}$ is optionally present at one or more of the phenyl ring carbon atoms, and is selected from the group consisting of
(1) halogen,
(2) hydroxy,
(3) cyano,
(4) —$(CH_2)_q$-aryl,
(5) —O—$(CH_2)_q$-aryl,
(6) —$C_{1-6}$ alkyl,
(7) —$OC_{1-6}$ alkyl,
(8) heteroaryl, wherein said heteroaryl is an aromatic cyclic group having from 5 to 12 cyclic atoms, said cyclic atoms selected from carbon, nitrogen, oxygen or sulfur,
(9) —$N(R^7R^8)$,
and wherein said alkyl, aryl or heteroaryl moiety is optionally substituted with one or more
(a) halogen,
(b) hydroxy,
(c) cyano,
(d) —$C_{1-6}$ alkyl, or
(e) —$OC_{1-6}$ alkyl.

11. A compound of claim 1, wherein the compound of formula (I) is a compound of formula (III):

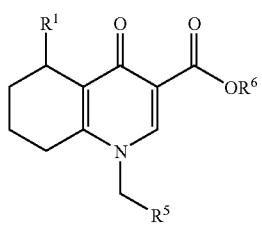

(III)

or a pharmaceutically acceptable salt thereof, wherein $R^1$, $R^5$ and $R^6$ are as defined in claim 1.

12. A compound of claim 1, wherein the compound of formula (I) is a compound of formula (IV):

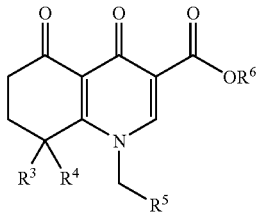

(IV)

or a pharmaceutically acceptable salt thereof, wherein $R^3$, $R^4$, $R^5$ and $R^6$ are as defined in claim 1.

13. A compound of claim 1, which is selected from the group consisting of
1-(Biphenyl-4-ylmethyl)-4-oxo-4,5,6,7-tetrahydro-1H-cyclopenta[b]pyridine-3-carboxylic acid;
1-[(2E)-3-(2-Fluorophenyl)prop-2-en-1-yl]-4,5-dioxo-1,4,5,6,7,8-hexahydroquinoline-3-carboxylic acid;
1-[(2Z)-3-(2-Fluorophenyl)prop-2-en-1-yl]-4,5-dioxo-1,4,5,6,7,8-hexahydroquinoline-3-carboxylic acid;
1-(Biphenyl-4-ylmethyl)-5-hydroxy-4-oxo-1,4,5,6,7,8-hexahydroquinoline-3-carboxylic acid;
(±)-5-Hydroxy-1-[(2'-methoxybiphenyl-4-yl)methyl]-4-oxo-1,4,5,6,7,8-hexahydroquinoline-3-carboxylic acid;
(±)-1-(Biphenyl-4-ylmethyl)-5-methoxy-4-oxo-1,4,5,6,7,8-hexahydroquinoline-3-carboxylic acid;
(±)-5-Hydroxy-5-methyl-1-(2-naphthylmethyl)-4-oxo-1,4,5,6,7,8-hexahydroquinoline-3-carboxylic acid;
(±)-1-(Biphenyl-4-ylmethyl)-5-ethyl-5-hydroxy-4-oxo-1,4,5,6,7,8-hexahydroquinoline-3-carboxylic acid;
(±)-5-benzyl-1-(biphenyl-4-ylmethyl)-5-hydroxy-4-oxo-1,4,5,6,7,8-hexahydroquinoline-3-carboxylic acid;
or a pharmaceutically acceptable salt thereof.

14. A pharmaceutical composition comprising a compound of any of claim 1, or a pharmaceutically acceptable salt thereof, and a pharmaceutically acceptable carrier.

15. A compound selected from the tables below:

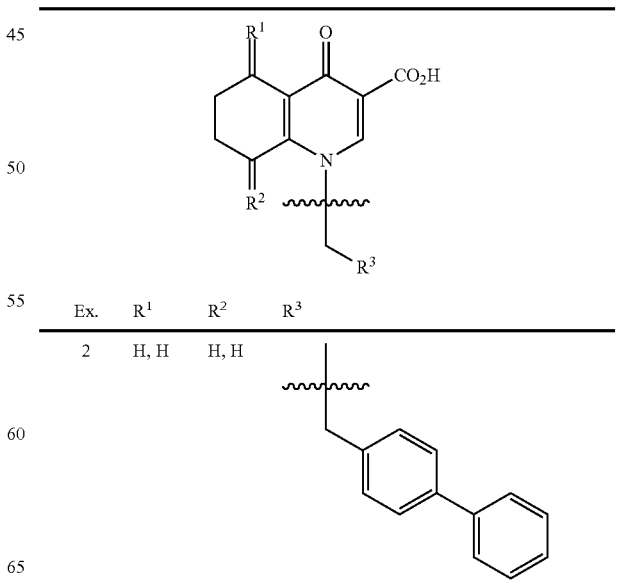

| Ex. | $R^1$ | $R^2$ | $R^3$ |
|---|---|---|---|
| 2 | H, H | H, H | (biphenyl-4-ylmethyl) |

-continued
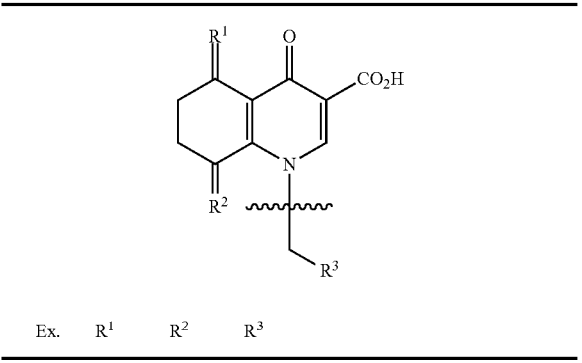
| Ex. | R¹ | R² | R³ |
|---|---|---|---|
| 3 | H, H | H, H | 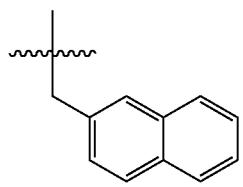 |
| 4 | H, H | H, H | 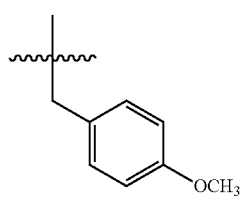 |
| 5 | H, H | H, H | 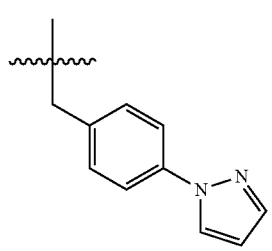 |
| 6 | O | H, H | 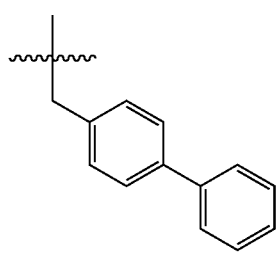 |
| 7 | O | H, H | 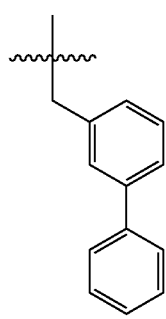 |
-continued
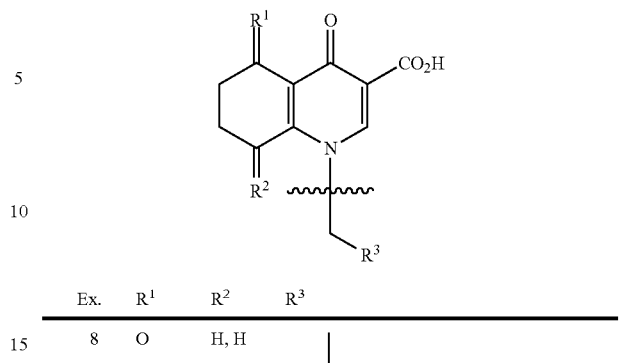
| Ex. | R¹ | R² | R³ |
|---|---|---|---|
| 8 | O | H, H | 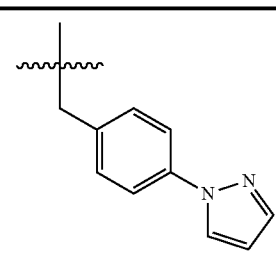 |
| 9 | O | H, H | 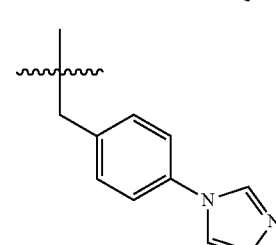 |
| 10 | O | H, H | 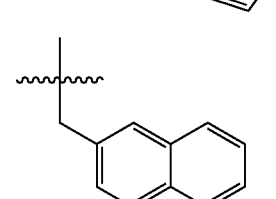 |
| 11 | O | H, H | 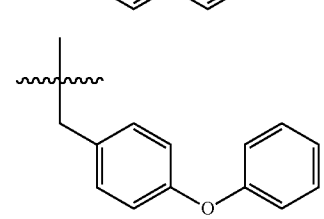 |
| 12 | O | H, H | 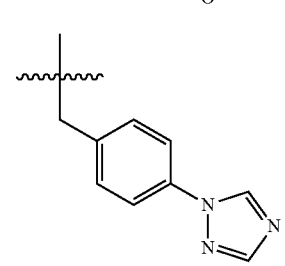 |
| 13 | H, H | O | 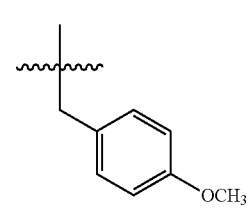 |

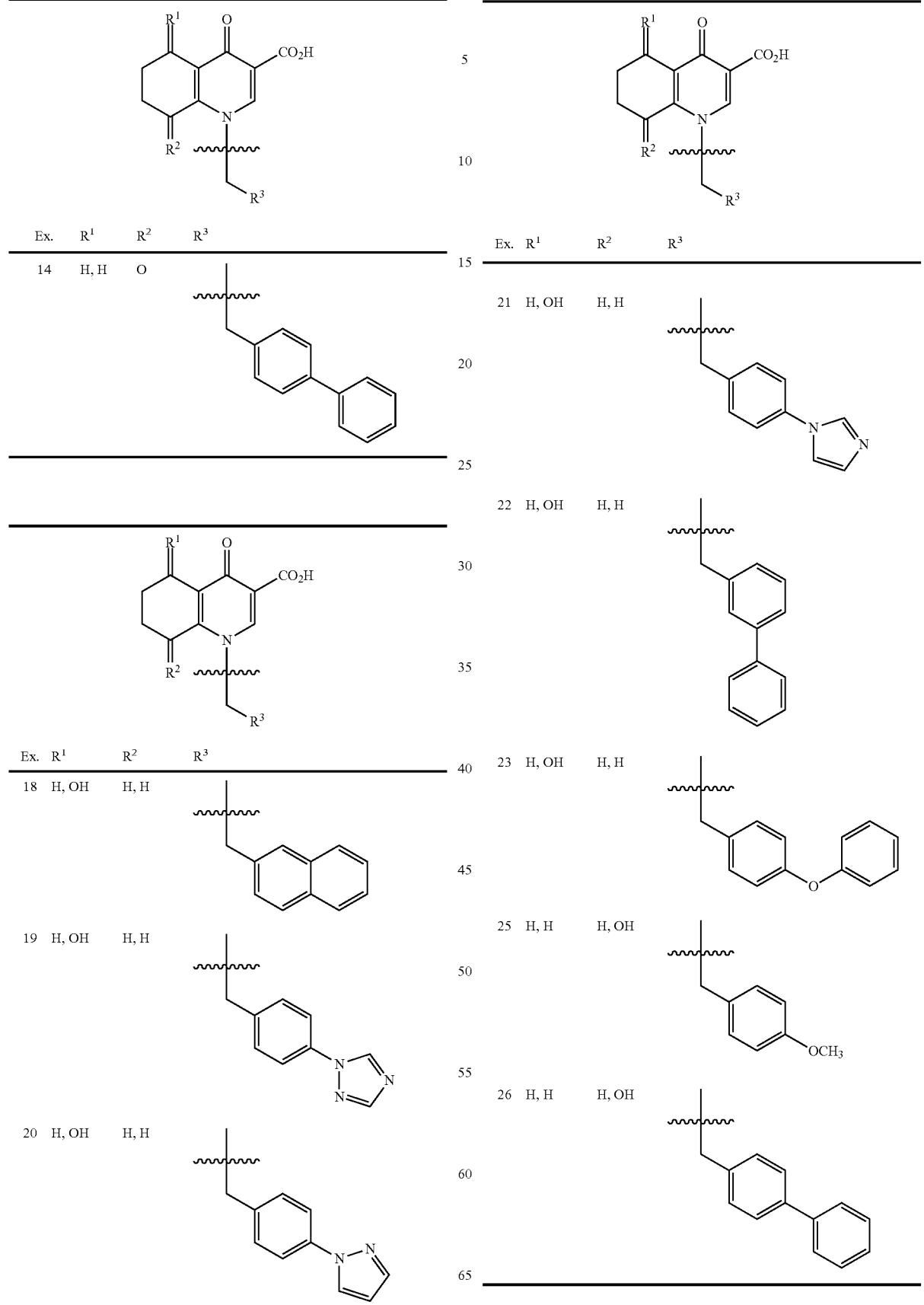

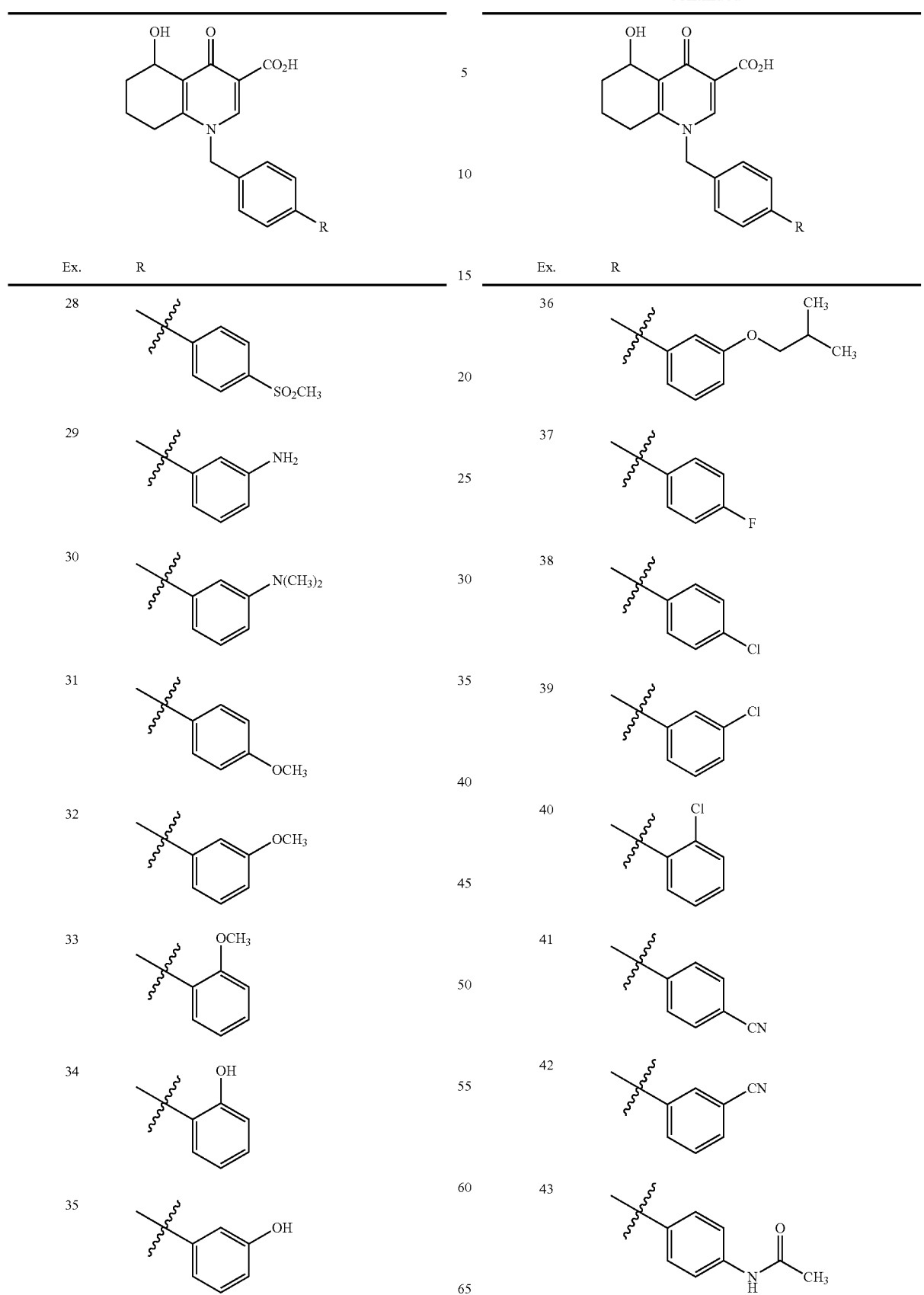

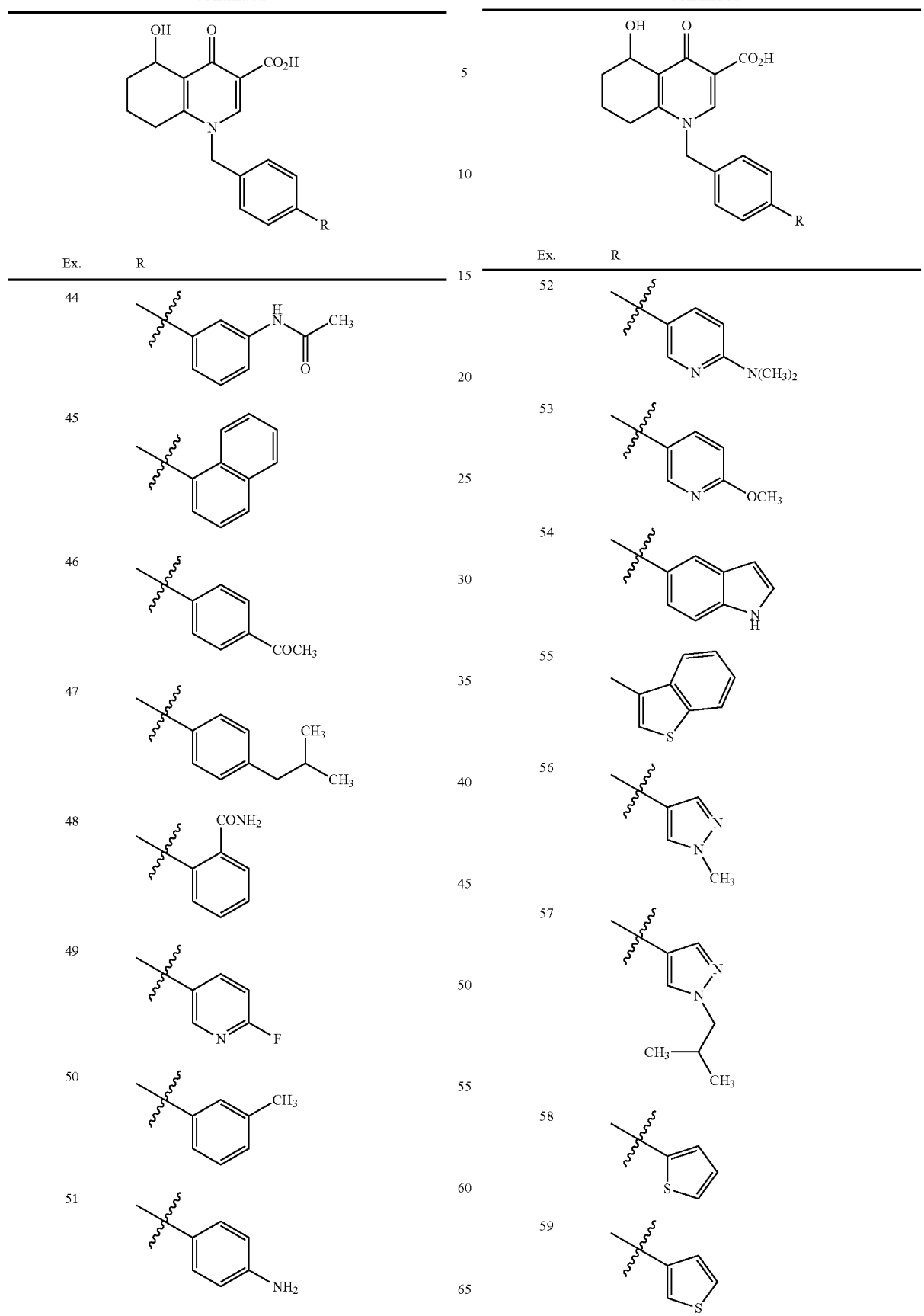

-continued
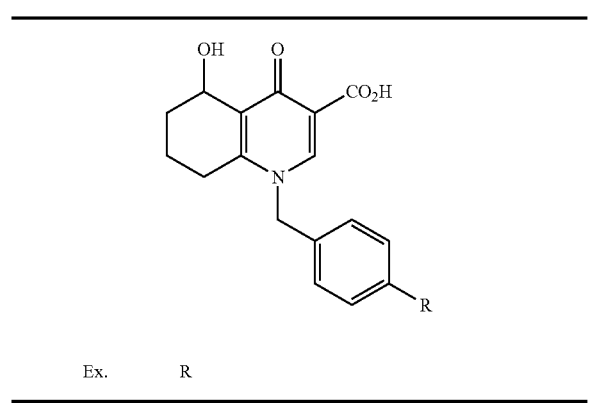
| Ex. | R |
|---|---|
| 60 | 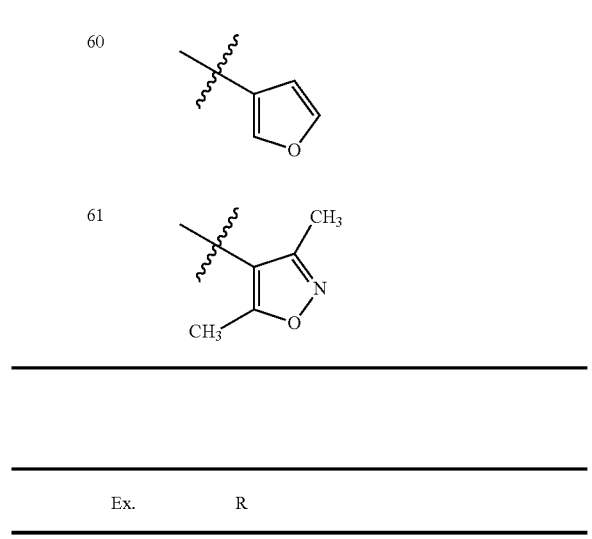 |
| 61 | |
| Ex. | R |
|---|---|
| 65 | 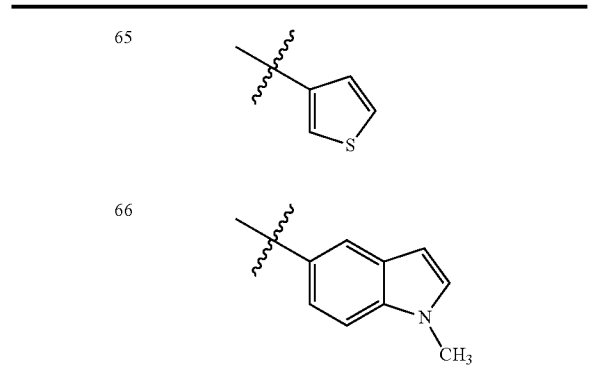 |
| 66 | |
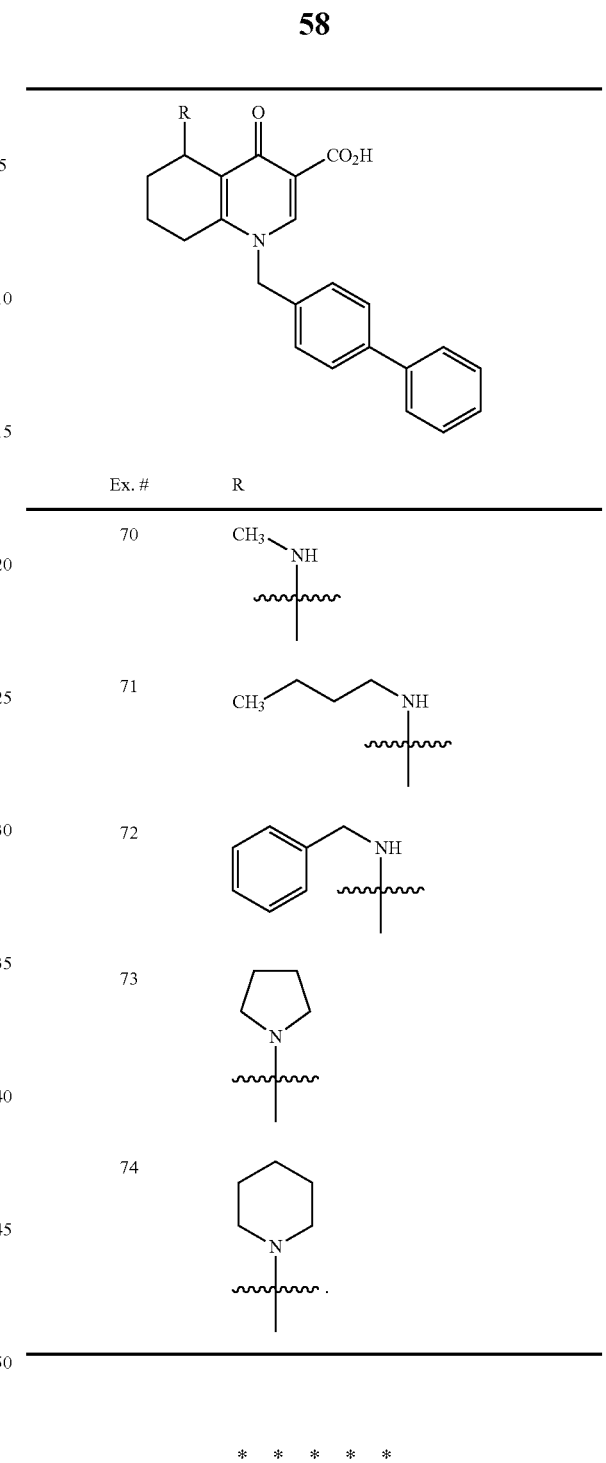
| Ex. # | R |
|---|---|
| 70 | CH₃-NH- |
| 71 | CH₃-(CH₂)₂-NH- |
| 72 | PhCH₂-NH- |
| 73 | pyrrolidinyl |
| 74 | piperidinyl |
* * * * *